(12) United States Patent
Kim et al.

(10) Patent No.: US 7,640,789 B2
(45) Date of Patent: Jan. 5, 2010

(54) ULTRA-SENSITIVE METAL OXIDE GAS SENSOR AND FABRICATION METHOD THEREOF

(75) Inventors: Il-Doo Kim, Seoul (KR); Jae-Min Hong, Seoul (KR); Dong-Young Kim, Seoul (KR); Seong-Mu Jo, Seoul (KR); Avner Rothschild, Haifa (IL); Harry L. Tuller, Wellesley, MA (US)

(73) Assignee: Korea Institute of Science and Technology (KR)

( * ) Notice: Subject to any disclaimer, the term of this patent is extended or adjusted under 35 U.S.C. 154(b) by 332 days.

(21) Appl. No.: 11/644,121

(22) Filed: Dec. 22, 2006

(65) Prior Publication Data

US 2007/0261959 A1  Nov. 15, 2007

(30) Foreign Application Priority Data

Dec. 23, 2005 (KR) ...................... 10-2005-0129096
Nov. 15, 2006 (KR) ...................... 10-2006-0113002

(51) Int. Cl.
*G01N 27/26* (2006.01)
*B05D 3/00* (2006.01)

(52) U.S. Cl. ........................ 73/31.06; 204/424; 427/190
(58) Field of Classification Search ................ 73/31.06; 204/424; 427/190
See application file for complete search history.

(56) References Cited

U.S. PATENT DOCUMENTS 5,330,833 A  *  7/1994  Yamashita et al. .......... 428/364

OTHER PUBLICATIONS

Katarzyna, S.M. et al., "Molybdenum and Tungsten Oxide Nanowires Prepared by Electrospinning", Mater. Res. Soc. Symp. Proc., vol. 847, 2005, pp. EE9.46.1-EE9.46.6.*
Gouma, P. et al., "Nano-Composite Metal Oxides for Electronic Noses", NSF Nanoscale Science and Engineering Grantees Conference, Dec. 13-15, 2004, pp. 1-3.*
Li, D. et al., "Direct Fabrication of Composite and Ceramic Hollow Nanofibers by Electrospinning", Nano Letters, vol. 4, No. 5, 2004, pp. 933-938.*
Wang, Y. et al., "Synthesis and Characterization of Ultra-Fine Tin Oxide Fibers Using Electrospinning", J. Am. Ceram. Soc., vol. 88, No. 8, 2005, pp. 2059-2063.*
Jeon, et al., "Dye-sensitized solar cell using elecrospun ZnO fiber mats," *IUPAC International Symposium on Advanced Polymers for Emerging Technologies*, pp. 578 (2006).
Kim, et al., "Ultrasensitive Chemiresistors Based on Electrospun $TiO_2$ Nanofibers," *Nano Letters*, vol. 6, No. 9, pp. 2009-2013 (2006).

* cited by examiner

*Primary Examiner*—Daniel S Larkin
(74) *Attorney, Agent, or Firm*—Darby & Darby P.C.; S. Peter Ludwig

(57) ABSTRACT

A method for fabricating an ultra-sensitive metal oxide gas sensor is disclosed, which comprises the steps of spinning a mixture solution including a metal oxide precursor and a polymer onto a sensor electrode to form a metal oxide precursor-polymer composite fiber; thermally compressing or thermally pressurizing the composite fiber; and thermally treating the thermally compressed or thermally pressurized composite fiber to remove the polymer from the composite fiber. Since the gas sensor includes a macro pore between nanofibers and a meso pore between nano-rods and/or nano-grains, gas diffusion and surface area can be maximized. Also, the ultra-sensitive sensor having high stability in view of mechanical, thermal, and electrical aspects can be obtained through rapid increase of adhesion between the metal oxide thin layer and the sensor electrode.

11 Claims, 22 Drawing Sheets

(c)

(d)

ULTRA-SENSITIVE METAL OXIDE GAS SENSOR AND FABRICATION METHOD THEREOF

BACKGROUND OF THE INVENTION

1. Field of the Invention

The present invention relates to an ultra-sensitive metal oxide gas sensor and a fabrication method thereof, and more particularly to a fabrication method of an ultra-sensitive metal oxide gas sensor, in which a fine structure of a metal oxide is a network structure of nanofibers composed of nanograins or nanorods composed of nanograins.

2. Description of the Background Art

When ZnO, $SnO_2$, $WO_3$ and $TiO_2$, which are metal oxide semiconductors, contacts special gas elements such as $H_2$, CO, $O_2$, $NO_x$, $CO_2$, DMMP, $CH_4$, $NH_3$, Alcohol and humidity, an electrical resistivity is changed by gas adsorption and oxidization/reduction occurring on the surface of the oxide.

Characteristics of a sensor fabricated by using the metal oxide semiconductor are considerably influenced by gas diffusivity and gas surface reaction. Accordingly, efforts have been made to increase an enhanced surface activity and a surface to volume ratio.

For example, studies of humidity and ammonia sensor using a ZnO nano wire structure have been made [Y. S, Zhang, Physica B-Condense Matter. Vol. 368, 94-99, 2005 or X. H. Wang, Appl. Phy. Lett. Vol. 252, 2504-2411, 2005]. Also, characteristics of a $SnO_2$ [Zhang, D. Nano Lett. 4, 1919, 2004] and $In_2O_3$ [Kolmakov, A. Nano Lett. 5, 667, 2005] sensor using nanowire have been studied [Sens. Actuators B, 108, 29, 2005].

A sensor using a single nanowire can obtain high sensitivity but has a problem in that it is difficult to fabricate a device having high reproducibility due to noise caused by unstability of contact resistance.

Thus, sensors fabricated using networks of nanofibers may offer high reproducibility and better electrical stability as compared to that of sensors using individual nanowire and nanofiber. Electrospinning is one of the most simple and versatile approaches offering the ability to produce multiple nanofiber networks.

The fiber prepared by the electrospinning has a diameter of a few tens nm to a few μm depending on preparation conditions. Therefore, a surface area per unit volume of electrospun nano fibrous mats is larger than that of a continuous film by a few hundreds times (two orders of magnitude). When the fiber is used as the sensor material, the sensor is expected to have high sensitivity and rapid response. In this respect, studies for use in a chemical sensor, an optical sensor, and a bio sensor have been made actively.

Electrospun nanofibrous mats having a diameter of several hundreds of micrometers, fabricated by electrospinning have been studied by various research groups [D. Li and Y Xia, Nano Lett. 3 (2003), 555]. Such electrospun nanofibrous mats have high gas diffusivity due to an excellent porous structure of an open pore structure. However, since the size of the nanofiber ranges a few hundreds nm, a specific surface area is very low, generally below 20 to 30 $m^2/g$. A sensor consisting of such materials enables fabrication of a large sized nanofiber, can obtain a network of an ultra-fine nanofiber at a low cost, and has sensing sensitivity more improved than that of a metal oxide nanowire obtained by thermal vapor deposition but still has deficient sensitivity.

There are increasing demands for a high sensitivity sensor of a thin layer of a fiber having an increased specific surface area of a metal oxide along with a porous structure having excellent gas diffusivity to attain a fast response time and high sensitivity sensing.

In addition, since adhesion between a metal oxide fiber and a sensing substrate is closely related to electrical contact, excellent adhesion is required to minimize noise. If a composite nanofiber including an electrospun metal oxide precursor is thermally treated on a metal or a ceramic substrate at a high temperature, peeling-off of nanofibers with respect to the substrate is observed.

SUMMARY OF THE INVENTION

Therefore, an object of the present invention is to provide an ultra-sensitive metal oxide gas sensor and a fabrication method thereof, in which a fine structure of a metal oxide has a nanorod and/or nanograin structure of excellent gas diffusivity and remarkably increased specific surface area, using thermocompression (hot pressing) to attain a fast response time and high sensitivity sensing, and adhesion between a porous metal oxide fiber and a sensor substrate is enhanced.

To achieve these and other advantages in accordance with the purpose of the present invention, as embodied and broadly described herein, there is provided an ultra-sensitive metal oxide gas sensor comprising a sensor electrode; and a porous metal oxide thin layer formed on the sensor electrode, having a network structure of nanofibers consisting of a single crystalline nano-rod. In this case, the porous metal oxide thin layer has a macro-pore between nanofibers and a meso-pore between nano-rods.

In another aspect of the present invention, there is provided an ultra-sensitive metal oxide gas sensor comprising a sensor electrode; and a porous metal oxide thin layer formed on the sensor electrode, having a network structure of nanofibers in which single crystalline nano-grains are conglomerated and twisted. In this case, the porous metal oxide thin layer has a macro-pore between nanofibers and a meso-pore between nano-grains.

In another aspect of the present invention, there is provided an ultra-sensitive metal oxide gas sensor comprising a sensor electrode; and a porous metal oxide thin layer formed on the sensor electrode, having a network structure of nano-rods consisting of nano-grains. In this case, the porous metal oxide thin layer has a meso-pore between nano-rods and a meso-pore between nano-grains.

In another aspect of the present invention, there is provided an ultra-sensitive metal oxide gas sensor comprising a sensor electrode; and a porous metal oxide thin layer formed on the sensor electrode, having a network structure of nanofibers consisting of at least one of nano-grain and nano-rod. The metal oxide thin layer includes ZnO, $SnO_2$, $VO_2$, $TiO_2$, $In_2O_3$, $CaCu_3Ti_4O_{12}$, NiO, $MoO_3$, $SrTiO_3$, $Fe_2O_3$, $TiO_2$ doped with at least one of Nb, Fe, Co, and V, $SrTiO_3$ doped with Fe, or ZnO doped with at least one of In and Ga.

In another aspect of the present invention, there is provided a method for fabricating an ultra-sensitive metal oxide gas sensor, comprising the steps of spinning a mixture solution including a metal oxide precursor and a polymer onto a sensor electrode to form a metal oxide precursor-polymer composite fiber; thermally compressing or thermally pressurizing the composite fiber; and thermally treating the thermally compressed or thermally pressurized composite fiber to remove the polymer from the composite fiber.

The metal oxide precursor includes a precursor constituting ZnO, $SnO_2$, $VO_2$, $TiO_2$, $In_2O_3$, $CaCu_3Ti_4O_{12}$, NiO, $MoO_3$, $SrTiO_3$, $Fe_2O_3$, a precursor constituting $TiO_2$ doped with at least one of Nb, Fe, Co, and V, a precursor constituting SrTiO$_3$ doped with Fe, or a precursor constituting ZnO doped with at least one of In and Ga.

The foregoing and other objects, features, aspects and advantages of the present invention will become more apparent from the following detailed description of the present invention when taken in conjunction with the accompanying drawings.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE PREFERRED EMBODIMENTS

Reference will now be made in detail to the preferred embodiments of the present invention, examples of which are illustrated in the accompanying drawings.

The present invention is characterized in that an ultrafine nanofiber (hereinafter, also referred to as "nanofiber") including fine nanofibrous is fabricated by electrospinning, and each nanofibrous is transformed into nanorod or nanograin by thermocompression or thermal pressurization so as to maximize a surface area, gas diffusion, and adhesion between metal oxide and electrode.

Figure 2:
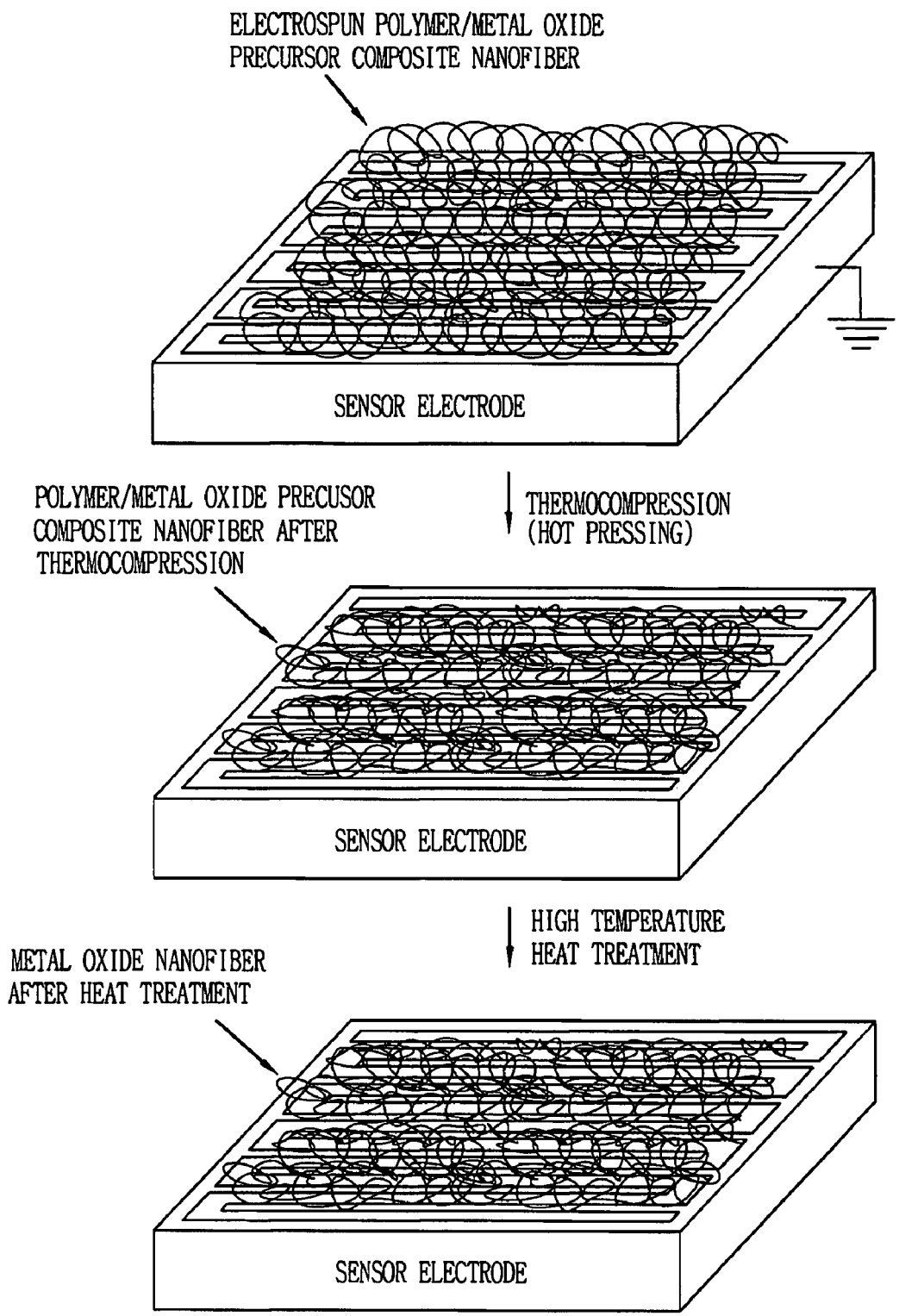
FIG. 2 illustrates electrospinning, thermocompression, and thermal treatment for fabrication of a sensor according to the present invention.

In more detail, referring to FIG. 2, a mixture solution including a metal oxide precursor, for example, a $TiO_2$, ZnO, or $SnO_2$ precursor, a polymer and a solvent is prepared, and then is spun on a sensor electrode to form a composite fiber of $TiO_2$/polymer, ZnO/polymer, or $SnO_2$/polymer, which is an ultrafine fiber, through phase separation between the metal oxide precursor ($TiO_2$, ZnO, or $SnO_2$ precursor) and polymer or mutual mixture.

Then, polymer is partially or totally melted with increasing a contact portion and contact area on a fiber through thermocompression or thermal pressurization of the composite fiber (in this case, if a portion and all of melting of the polymer is induced, a heating at a temperature a little higher than a glass transition temperature may be included), so that adhesion with electrode is enhanced.

The polymer is removed from the composite fiber through thermal treatment to obtain a porous thin layer including nanofiber of $TiO_2$ nanorod, ZnO nanofiber composed of nanograin, or $SnO_2$ nanorod composed of nanograin.

Such a porous metal oxide (for example, $TiO_2$, ZnO, and $SnO_2$) thin layer is formed on a sensor electrode such as Pt, Au, Pd, Ir, Ag, Rh, Ru, Ni, stainless steel, Al, Mo, Cr, Cu, or W electrode formed on a ceramic substrate, ITO (in doped $SnO_2$) or FTO (F doped $SnO_2$) electrode formed on a glass substrate, or a metal electrode formed on a plastic substrate or Si wafer, so that the thin layer can be used for a gas sensor.

Figure 3:
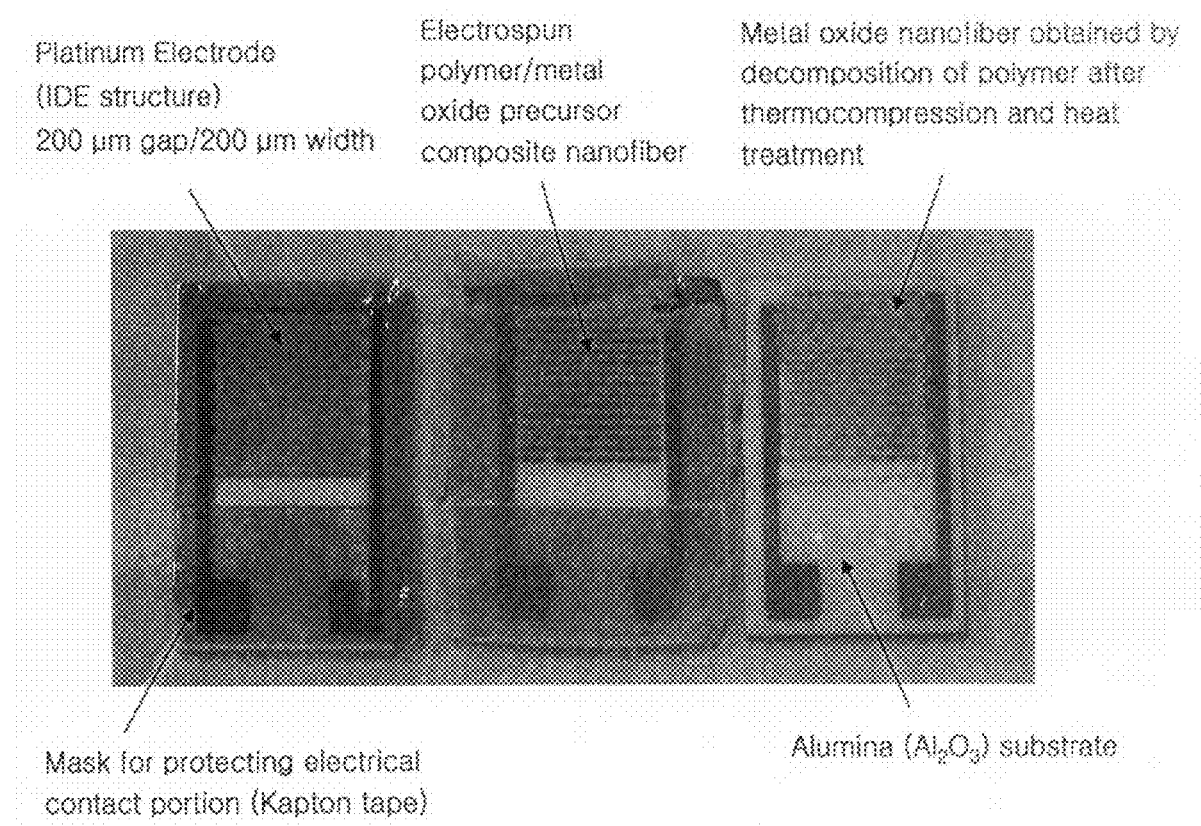
FIG. 3 illustrates images of a prototype test sensor device using a TiO$_2$ metal oxide nanofiber fabricated by performing electrospinning, thermocompression, and thermal treatment on a sensor electrode formed on an alumina substrate.
Figure 4:
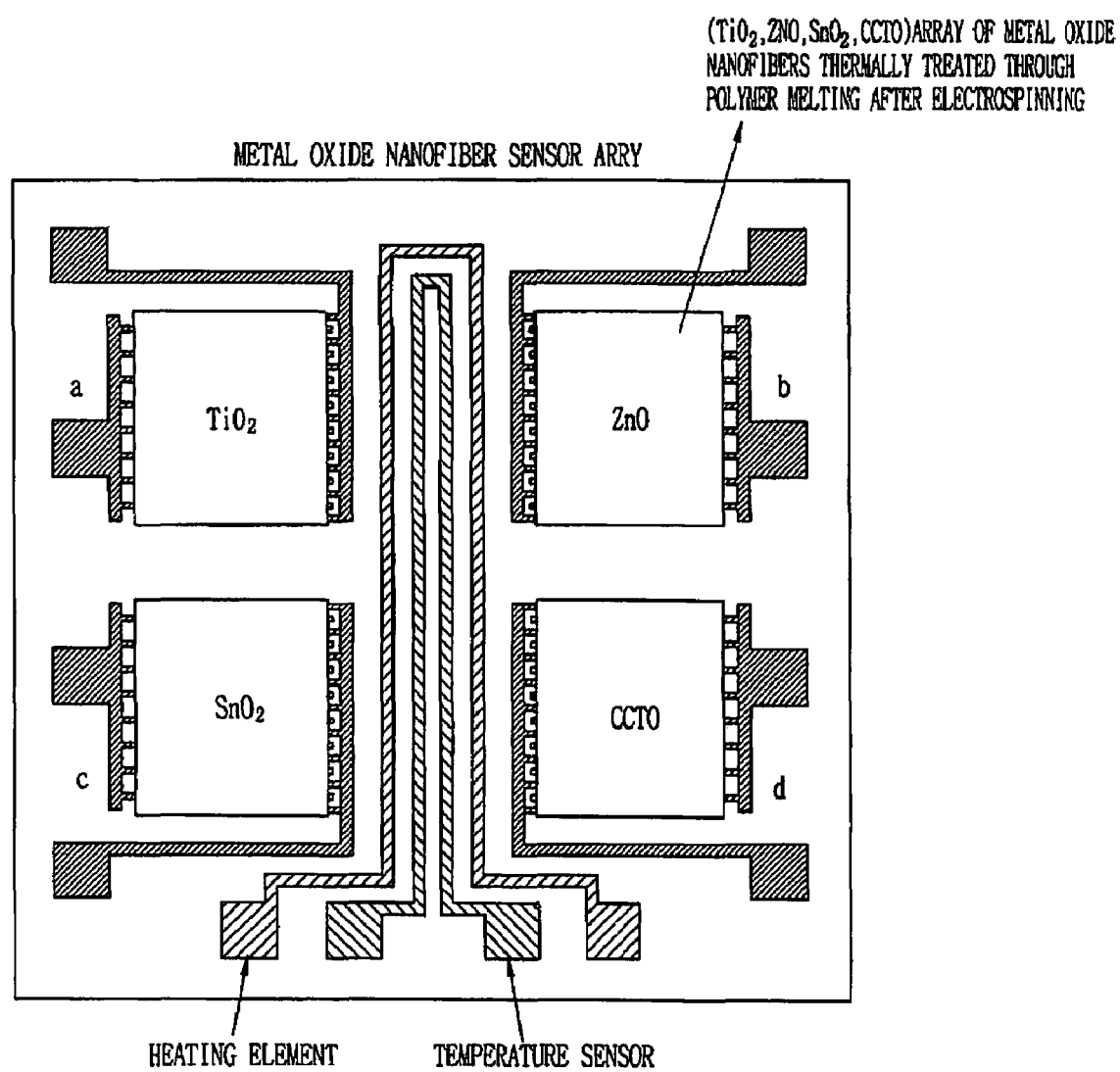
FIG. 4 illustrates an array sensor using a nanofiber mats fabricated by electrospinning, thermocompression, and thermal treatment for different kinds of metal oxides on a sensor electrode having an array sensor structure, provided with a high temperature heater, wherein examples of the metal oxide nanofiber sensor include ZnO, SnO$_2$, TiO$_2$, CaCu$_3$Ti$_4$O$_{12}$.

FIG. 3 illustrates images of a prototype test sensor device using a $TiO_2$ metal oxide nanofiber fabricated by electrospinning, thermocompression, and thermal treatment as shown in FIG. 2, and FIG. 4 illustrates an array sensor using nanofiber mats fabricated by electrospinning, thermocompression, and thermal treatment for different kinds of metal oxides on a sensor electrode having an array sensor structure, provided with a high temperature heater, wherein examples of the metal oxide nanofiber sensor include ZnO, $SnO_2$, $TiO_2$, and $CaCu_3Ti_4O_{12}$. Since oxidation/reduction reaction range of a metal oxide semiconductor selectively depends on kinds of the metal oxide semiconductor, various kinds of the metal oxide semiconductors are prepared in an array type for qualitative analysis of various reaction gases to enhance accuracy. Thus, resistance response, which is generated during reaction with external noxious gases such as $H_2$, $O_2$, CO, NOx, alcohol, $NH_3$, $CH_4$, SOx, DMMP, phenol, acetone, and formaldehyde, can be measured with ultra high sensitivity. At this time, a substrate provided with a micro heater therein may be used for better response with gas. The heater can externally be controlled for temperature control to highly enhance response with gas. In this case, Si wafer or glass substrate may be used as the substrate. There is no specific limitation in a lower electrode structure if an array electrode structure (IDC: interdigitated electrode structure) or parallel plate structure that can sense resistance response is made. Also, for the fabrication of the array sensor structure, thermocompression and thermal pressurization may be performed simultaneously after spinning of different mixture solutions.

Hereinafter, an ultra-sensitive metal oxide gas sensor and a fabrication method thereof according to the present invention will be described with reference to the accompanying drawings. In the embodiments of the present invention, electrospinning is used to obtain an ultrafine fiber. However, the present invention is not limited to electrospinning, and meltblown, flash spinning, and electrostatic melt-blown may be used.

Fabrication of Electrospinning Solution

In accordance with the present invention, an electrospinning solution obtained by mixing a Sol-Gel precursor of inorganic oxide with a polymer solution is used for the electrospinning. The polymer serves to increase viscosity of the solution to form fiber phases in the spinning, and control the structure of the spun fiber by miscibility with the inorganic oxide precursor.

The metal oxide precursor (hereinafter, also referred to as "inorganic oxide") used in the present invention is a precursor containing ions such as Zn, Sn, V, Ti, In, Ca, Cu, Ni, Mo, Sr, Fe, Nb, Co, and Ga. There is no specific limitation in a precursor if the precursor can form oxide, such as ZnO, $SnO_2$, $VO_2$, $TiO_2$, $In_2O_3$, $CaCu_3Ti_4O_{12}$, NiO, $MoO_3$, $SrTiO_3$, $Fe_2O_3$, $TiO_2$ doped with Nb, Fe, Co, and V, $SrTiO_3$ doped with Fe, or ZnO doped with In and Ga, through thermal treatment at high temperature (more than 200° C.) after response with the polymer. For example, titanium (IV) propoxide can be used as the $TiO_2$ precursor, zinc acetate can be used as the ZnO precursor, and tin acetate can be used as the $SnO_2$ precursor. The electrospinning solution is fabricated by using the sol-gel response of the inorganic oxide.

The polymer used in the present invention may be at least one selected from polyurethane copolymer containing polyurethane and polyetherurethane, cellulose inducer such as cellulose acetate, cellulose acetate butylate, and cellulose acetate propionate, polymethylmethacrylate (PMMA), polymethylacrylate (PMA), polyacryl copolymer, polyvinylacatate (PVAc), polyvinyl acetate copolymer, polyvinyl alcohol (PVA), polyperfluoroacrylate (PPFA), polystyrene (PS), polystyrene copolymer, polyethylene oxide (PEO), poly(phenylene oxide) (PPO), polyethylene oxide copolymer, polypropylene oxide copolymer, polycarbonate (PC), polyvinyl chloride (PVC), polycaprolactone, polyvinylpyrrolidone (PVP), polyvinylfluoride, polyvinylidenfluoride copolymer, and polyamide. However, the polymer is not limited to the above examples, and any kinds of the polymers that can form an ultrafine fiber through electrospinning may be used.

The polymer used in the present invention may be divided into a polymer having excellent miscibility with a metal oxide precursor and a polymer having bad miscibility with a metal oxide precursor. Examples of the polymer having excellent miscibility with a metal oxide precursor include PVAc, polyvinylpyrrolidone, polyvinylalcohol, and polyethyleneoxide. If electrospinning is performed using such a polymer, phase separation slowly occurs to generate a sol-gel reaction, which will be described later. Examples of the polymer having bad miscibility with a metal oxide precursor include polystyrene. If electrospinning is performed using such a polymer, it is difficult to maintain phase equilibrium and the polymer is rapidly solidified due to low miscibility with a metal oxide precursor. However, the polymer with bad miscibility with a metal oxide precursor may be used in the present invention. This will be described in the fifth embodiment of the present invention.

One example of the process of preparing the electrospinning solution will now be described in detail. First, polyvinyl acetate having great affinity with $TiO_2$, ZnO or $SnO_2$ is dissolved in dimethylformamide, acetone, tetrahydrofuran, toluene, or a mixed solvent thereof, and a polymer solution of 5~20% by weight, which generates viscosity suitable for formation of a fiber using electrospinning, is fabricated. A polymer having an average molecular weight in the range of 100,000 to 1,500,000 g/mol is used as polyvinyl acetate.

Thereafter, titanium propoxide is added to the polyvinyl acetate polymer solution in the range of 1 to 60 wt % of the polymer solution, and acetic acid is added as a catalyst to titanium propoxide, zinc acetate or tin acetate in the range of 0.01~60 wt %. The resulting solution is reacted at the normal temperature for 1 to 10 hours, and used as the electrospinning solution.

Fabrication of Ultrafine Fiber

An ultrafine metal oxide ($TiO_2$, ZnO or $SnO_2$) fiber is fabricated by using the prepared electrospinning solution and an electrospinning device.

Figure 1:
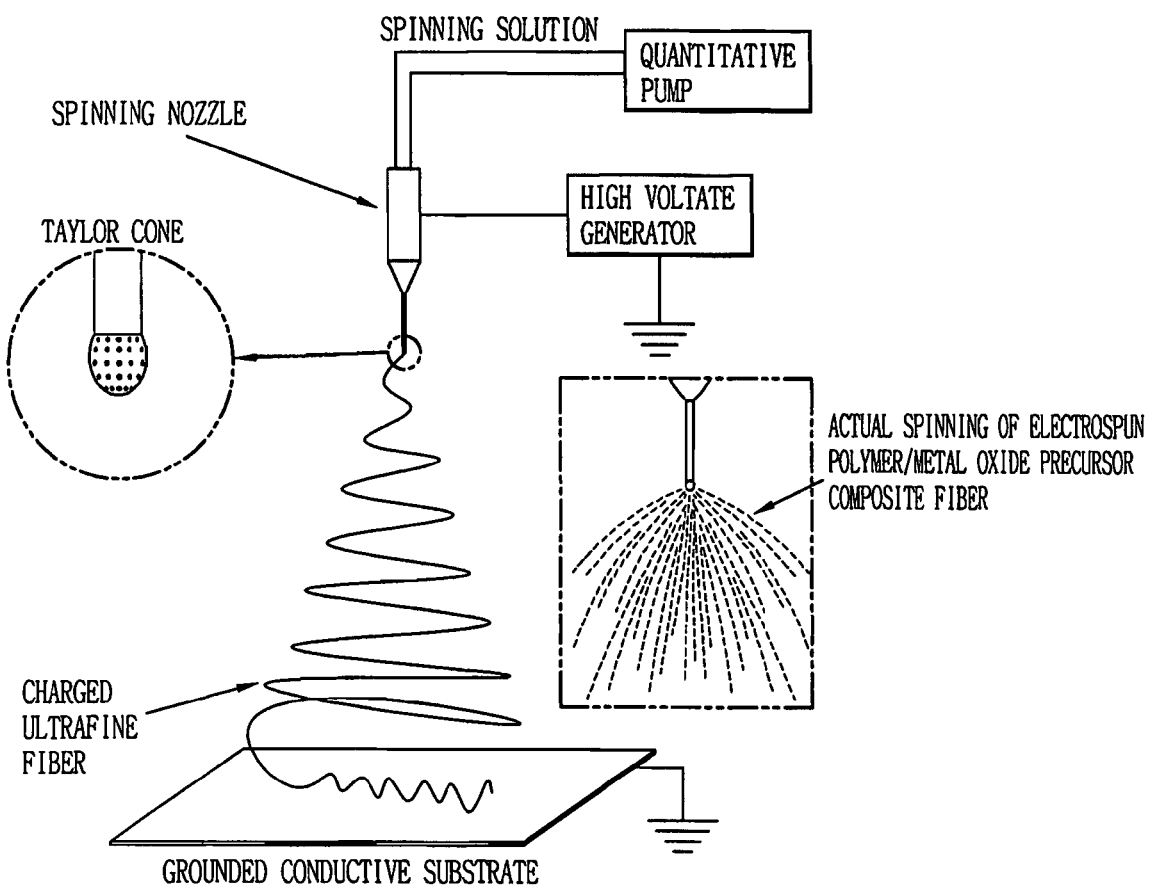
FIG. 1 is a schematic view illustrating an electrospinning device used in the present invention.

Referring to FIG. 1, the electrospinning device includes a spinning nozzle connected to a quantitative pump for quantitatively injecting a spinning solution, a high voltage generator, and an electrode on which a spun fiber layer is formed. According to use of purposes, a grounded metal plate (for example, a substrate on which a metal electrode such as Pt, Au, Pd, Ir, Ag, Rh, Ru, Ni, Cr, Mo, stainless steel, Al, Cu, and W is formed), a glass substrate coated with a transparent conductive oxide electrode (for example, ITO or FTO), or a plastic substrate on which a metal electrode is formed is used as a cathode, and the spinning nozzle having a pump which can control a discharge quantity per hour is used as an anode. The ultrafine fiber having a thickness of 50 to 1000 nm is fabricated on the electrode (or substrate) by applying 10 to 30 kV to the high voltage generator and controlling a solution discharge speed of the spinning nozzle to 10 to 50 µl/minute. The electrospinning is carried out until the film consisting of the ultrafine metal oxide fiber is formed on the substrate at a thickness of 0.1 to 20 µm.

The electrospun inorganic oxide/polymer composite fiber is accompanied by a complicate forming process. As shown in FIG. 1, the spinning solution is sprayed through the spinning nozzle electrified by the high voltage generator, and drawn to the grounded conductive substrate by an electric field. A jet flow of the spinning solution is generated from the spinning nozzle to the grounded substrate. The jet flow is formed in a conical shape and called Taylor cone. When spinning is started from the Taylor cone having a large amount of positive charges formed by the spinning nozzle of the electrospinning device, a Sol state of an inorganic oxide precursor is converted into a Gel state by reaction with moisture of the air.

With the Sol-Gel conversion, the spinning is accelerated, the diameter of the fiber is thinned, the surface area thereof is enlarged, and the used solvent is volatilized. In this process, with the foregoing chemical reaction, a concentration of the solution is rapidly changed. In addition, a temperature of the surface of the fiber is lowered by volatilization of the solvent, and moisture of the air is condensed to change the degree of the Sol-Gel conversion. Especially, since the electrospinning using the inorganic oxide-polymer mixed solution is influenced by moisture, the ambient temperature and humidity of the electrospinning device are very important process parameters.

In the electrospinning process, the Sol-Gel reaction of the metal oxide (for example, $TiO_2$, ZnO, $SnO_2$, $TiO_2$ doped with Nb, or $CaCu_3Ti_4O_{12}$) precursor contained in the spinning solution discharged from the spinning nozzle is carried out by moisture. In the preparation process of the spinning solution, some of the precursor is mixed with the polymer solution in a Sol type of $TiO_2$, ZnO, $SnO_2$, $TiO_2$ doped with Nb, or $CaCu_3Ti_4O_{12}$ due to hydrolysis generated by an acid catalyst. When the spinning is started, the gelation is accelerated. With the gelation, the discharged spinning solution is thinned for a short time. Here, the surface area of the fiber is considerably increased to volatilize the solvent. The phase separation is started on the metal oxide precursor and the polymer solution having a thermodynamically miscible state due to rapid concentration change and gelation. In this process, miscibility of the polymer and the $TiO_2$, ZnO, $SnO_2$, $TiO_2$ doped with Nb, or $CaCu_3Ti_4O_{12}$ precursor has great influence on the structure of the electrospun fiber.

In the case of a polymer having excellent miscibility, for example, polyvinyl acetate (PVAc) or polyvinyl pyrolidon (PVP), the phase separation is slowly performed so that a $TiO_2$, ZnO, $SnO_2$, $TiO_2$ doped with Nb, or $CaCu_3Ti_4O_{12}$ domain and a polyvinyl acetate domain can coexist with mobility. At this time, temperature drop of the surface of the fiber by rapid volatilization of the solvent condenses the ambient moisture, and thus the gelation differently occurs in the fiber and on the surface of the fiber.

In addition, when each domain has mobility, a specific structure is obtained by thermal treatment depending on the drawn range of the domains, the types of the metal oxide precursor, and the types of the used polymer in the spinning process. Especially, according to the structure, mobility of each domain may be changed through thermal compression (pressurization) before and after the glass transition temperature of the polymer after the electrospinnning of the metal oxide/polymer composite fiber, adhesion with the substrate may be improved through partial and entire melting of the used polymer, and density per unit volume and specific surface area may be improved greatly after thermal treatment. This structure is a very important parameter for application of the sensor using the ultrafine fiber. The main technical feature of the present invention is to allow the nanofiber of the metal oxide semiconductor to become a fine nanofiber having excellent adhesion through thermocompression. The nanofiber of the metal oxide semiconductor, which has not undergone thermocompression, is easily peeled off from the sensor substrate, thereby causing unstable measurement of the sensor or making measurement of the sensor impossible.

Fabrication of Metal Oxide Nanorod and/or Nanofiber

The electrode or substrate on which the electrospun ultrafine fiber is formed is pressed and thermally compressed under the pressure of 1.5 Kgf/cm$^2$ (213.4 psi based on 1.5 Ton, 10 cm×10 cm electrode substrate) at a temperature more than the glass transition temperature of the used polymer (120° C. if polyvinylacetate is used as the polymer) for 10 minutes. The pressure, temperature, and time for the thermocompression can properly be selected considering the types of the used polymer and the glass transition temperature of the polymer. If the heat treatment is applied at a temperature more than the glass transition temperature of the polymer, it is possible to apply heat without compression to the substrate or to pressurize the substrate using hot compressed air. In this process, mobility between the precursor phase-separated during electrospinning and the polymer is controlled, and a nanograin and/or nanorod structure is obtained after thermal treatment.

Figure 6:
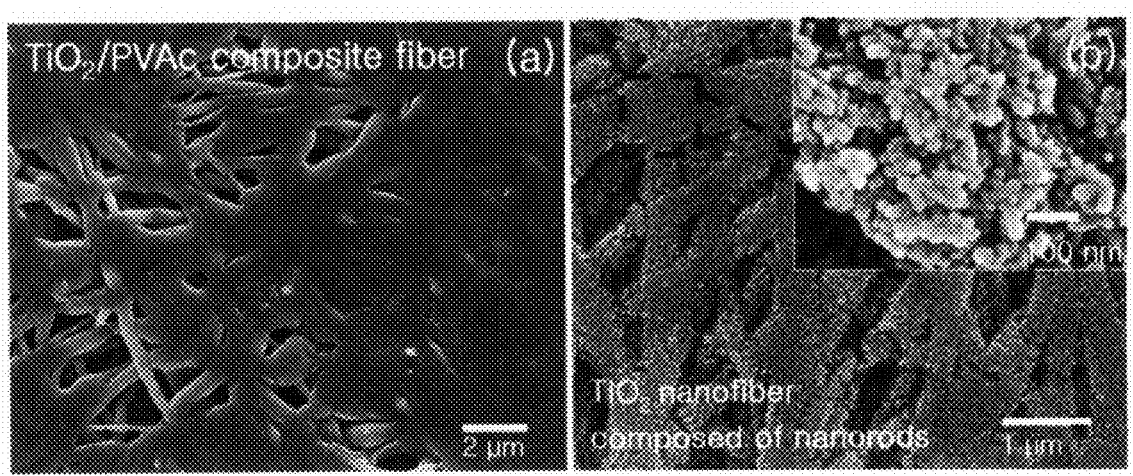
FIG. 6 illustrates (a) a SEM image of a TiO$_2$/PVAc composite fiber obtained by thermocompression under the pressure of 1.5 Kgf/cm$^2$ (213.4 psi) at 120° C. for 10 minutes in accordance with the first embodiment of the present invention. Thermal compression is introduced to drive the polymer (PVAc) above its glass transition temperature resulting in markedly better adhesion due to the partial or entire melting of PVAc. Subsequent heat treatment resulted in nanofibers consisting of nanorods as shown in FIG. 6(b). The adhesion is markedly enhanced. The inset of FIG. 6(b) exhibits the microstructure of nanorods.
Figure 13:
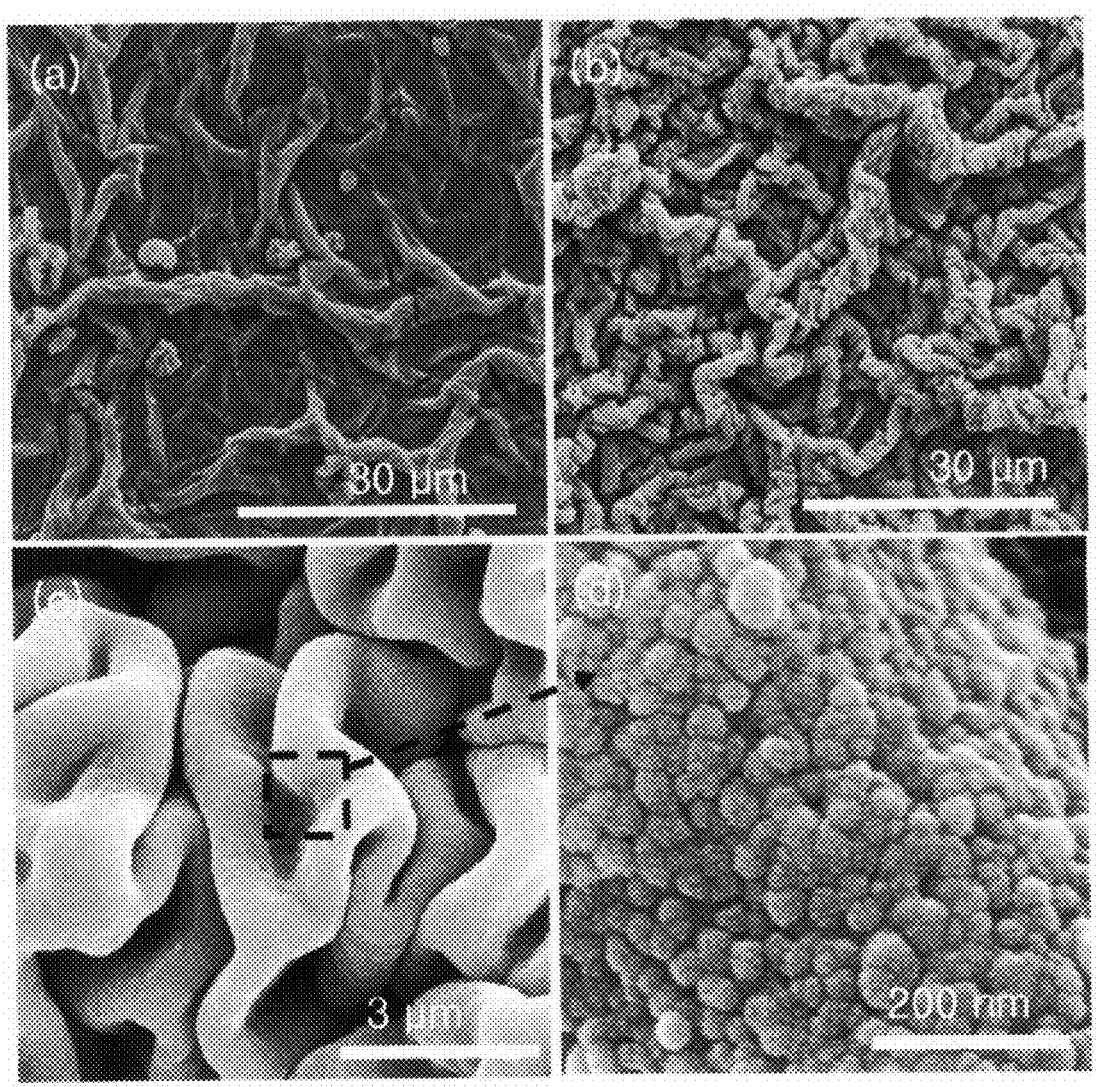
FIG. 13(a) to (d) illustrate SEM images of ZnO obtained by thermal treatment of a ZnO/PVAc composite fiber shown in FIG. 12(a) at 450° C. for 30 minutes after thermocompression under the pressure of 1.5 Kgf/cm$^2$ (213.4 psi) at 120° C. for 10 minutes in accordance with the second embodiment of the present invention.
Figure 18:
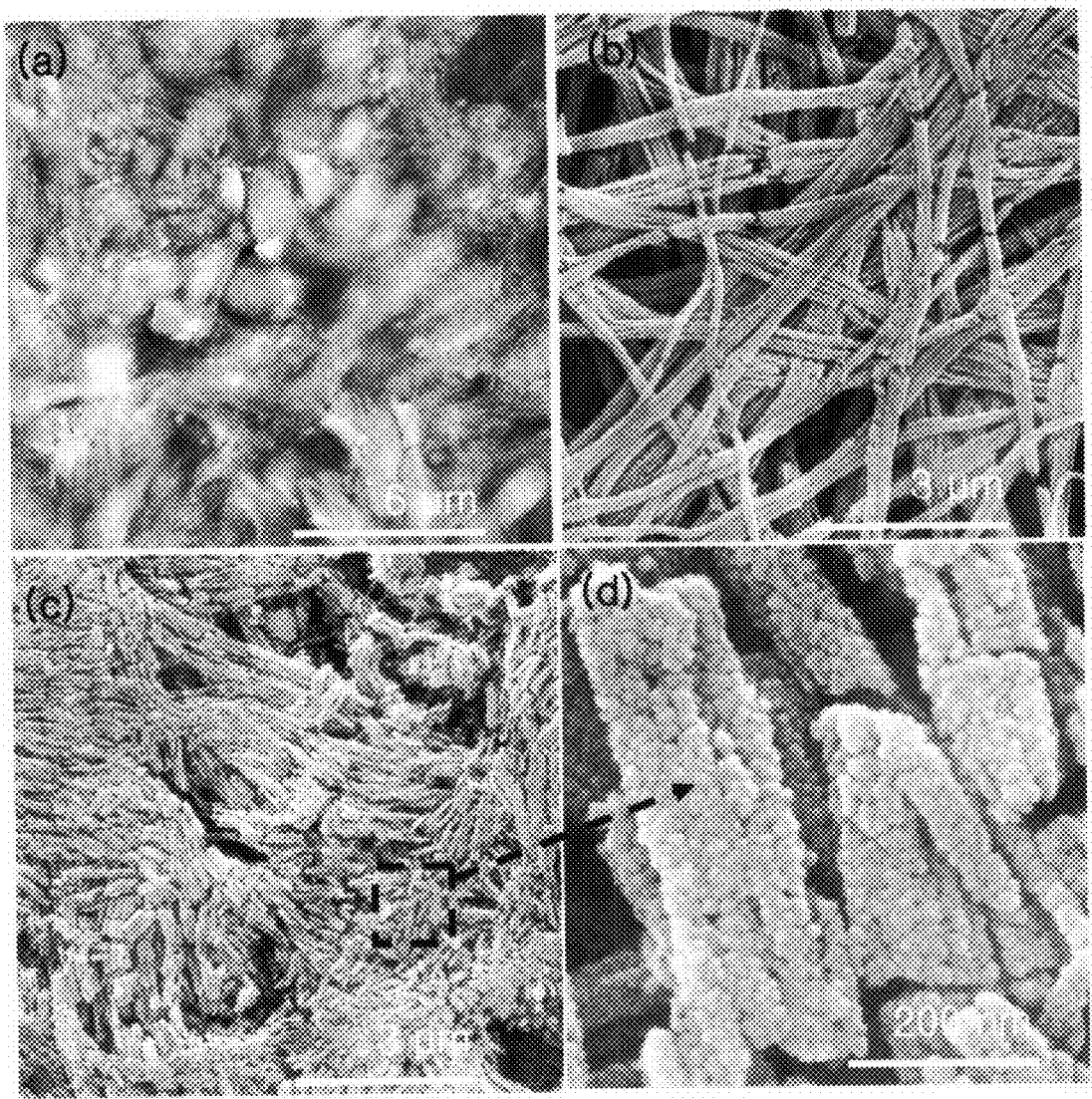
FIG. 18(a) to (d) illustrate SEM images of SnO$_2$ obtained by thermal treatment of a SnO$_2$/PVAc composite fiber shown in FIG. 17(a) at 450° C. for 30 minutes after thermocompression under the pressure of 1.5 Kgf/cm$^2$ (213.4 psi) at 120° C. for 10 minutes in accordance with the third embodiment of the present invention.
Figure 20:
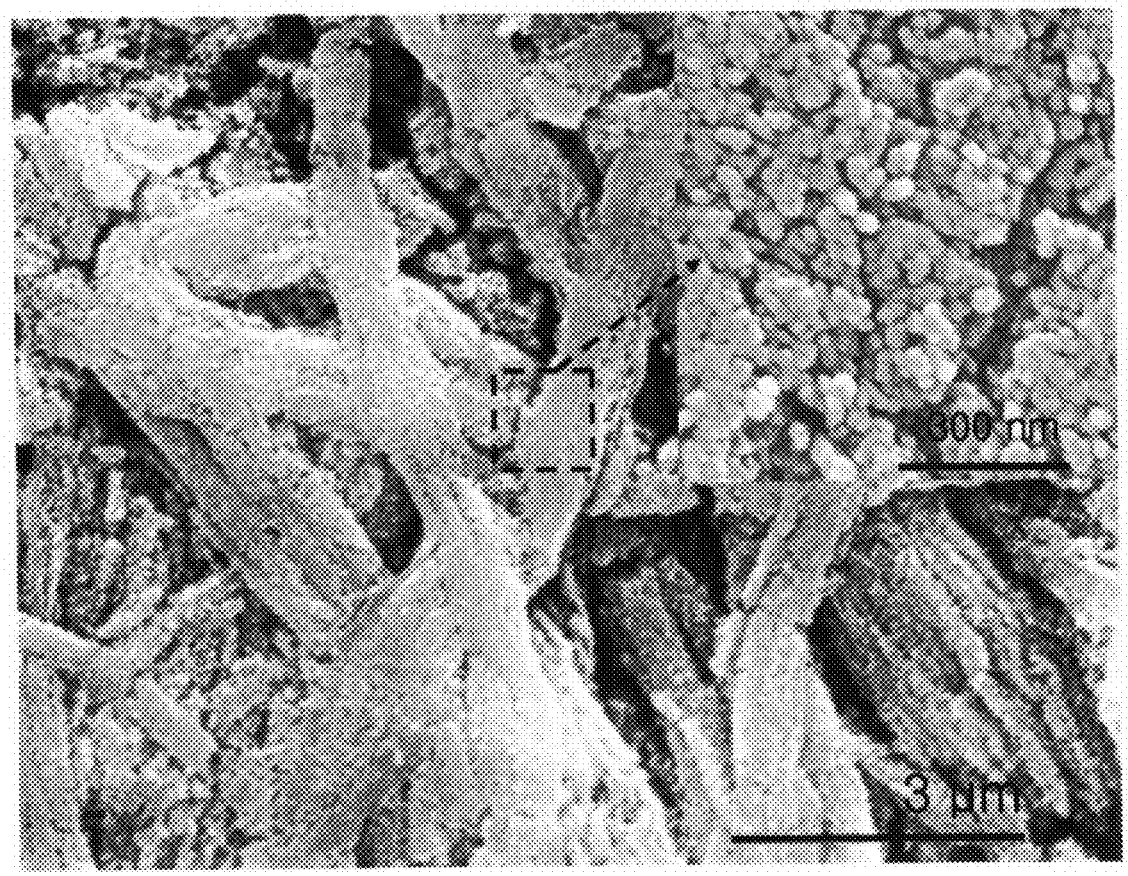
FIG. 20 illustrates a SEM image of a doped metal oxide nanorod, for example, a TiO$_2$ nanorod doped with Nb (Nb doped TiO$_2$) in accordance with the fourth embodiment of the present invention.
Figure 22:
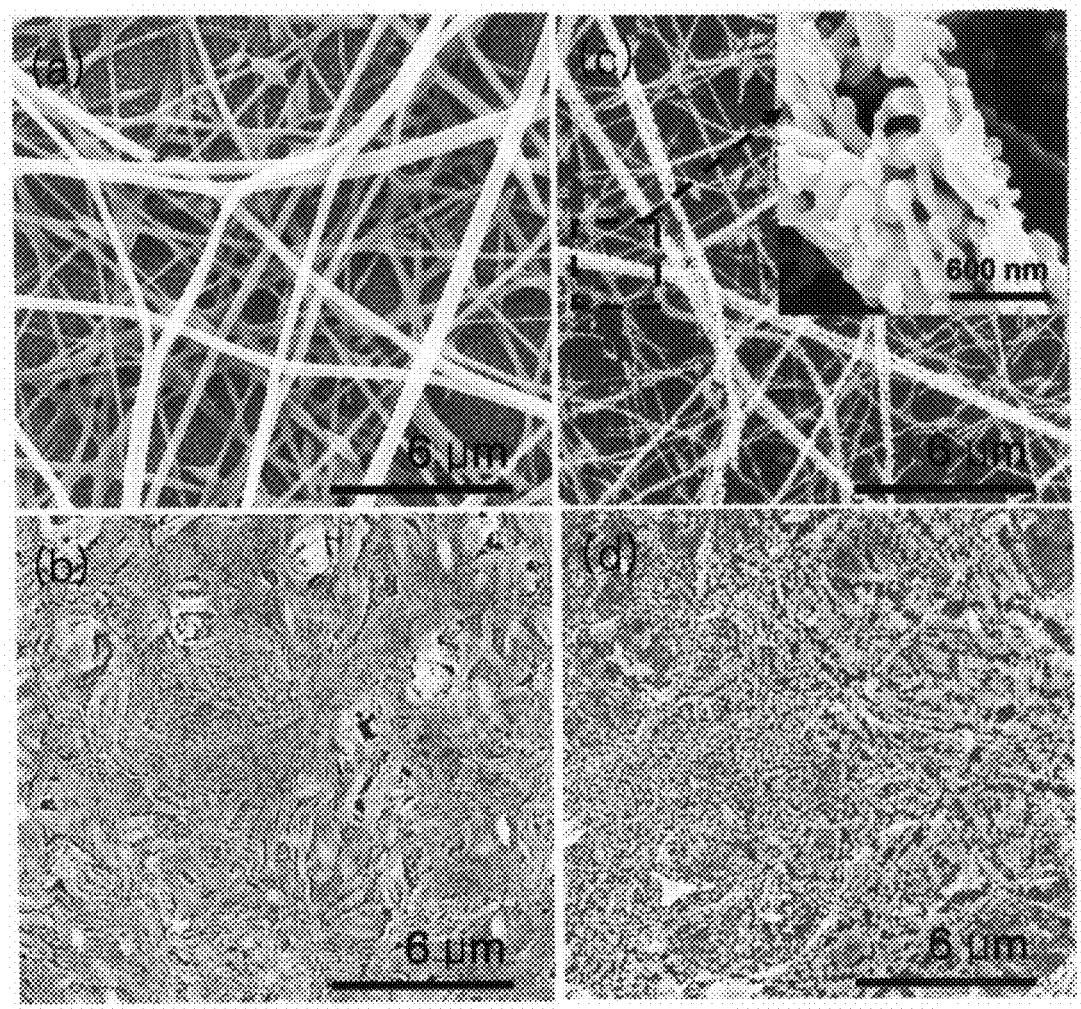
FIGS. 22(a) and (b) illustrate SEM images of CaCu$_3$Ti$_4$O$_{12}$ (CCTO) surface thermally treated at 450° C. before and after thermocompression using FTO (F doped SnO$_2$) electrode, and (c) and (d) illustrate SEM images of CCTO surface thermally treated at 800° C. before and after thermocompression using Pt electrode.

The polymer is removed in such a manner that the polymer is dissolved by thermal treatment at 450° C. for 30 minutes after thermocompression. In this case, a $TiO_2$ nanofiber composed of single crystalline nanorods as shown in FIG. 6(b), a twist-typed ZnO nanofiber composed of conglomerate nanograins as shown in FIG. 13(b), a $SnO_2$ nanorod composed of nanograins as shown in FIG. 18(d), a Nb doped $TiO_2$ nanorods including nanograins as shown in FIG. 20, a $CaCu_3Ti_4O_{12}$ nanofiber composed nanograins and nanorods as shown in FIG. 22(d), and the like are obtained. As shown, the present invention is characterized in that a nanofiber having a fine pore and a macro pore is fabricated by the process that ultrafine fiber phase is converted into nanograin or nanorod through thermocompression and thermal treatment. The temperature and time for thermal treatment after thermocompression are determined considering crystallization and plastic temperature. Thermal treatment may be performed in the range of 200~800° C. depending on the types of the metal oxide precursor.

COMPARABLE EXAMPLE 1

Thermal Treatment without Thermocompression after Electrospinning of a Mixture Solution of Polyvinyl Acetate and $TiO_2$ Precursor Titanium propoxide of 6 g was slowly added at the normal temperature to a polymer solution prepared by dissolving polyvinyl acetate (Mw: 850,000) of 30 g in a mixed solvent of acetone of 270 ml and dimethylformamide of 30 ml. With the reaction by moisture of the solvent, the resulting solution became a suspension. Acetic acid of 2.4 g was slowly dropped as a reaction catalyst. With the reaction, the suspension became a transparent solution.

The electrospinning was carried out by using the electrospinning device of FIG. 1. The Pt-coated $Al_2O_3$ substrate was used as a cathode, and the metal needle connected to the pump controlling the discharge speed was used as an anode. Voltage of 15 kV was applied between the two electrodes. The discharge speed of the spinning solution was controlled to 30 μl/minute. The electrospinning was performed until the total discharge amount became 5,000 μl, thereby forming an ultrafine $TiO_2$-polyvinyl acetate composite fiber layer on the Pt-coated $Al_2O_3$ substrate.

Figure 5:
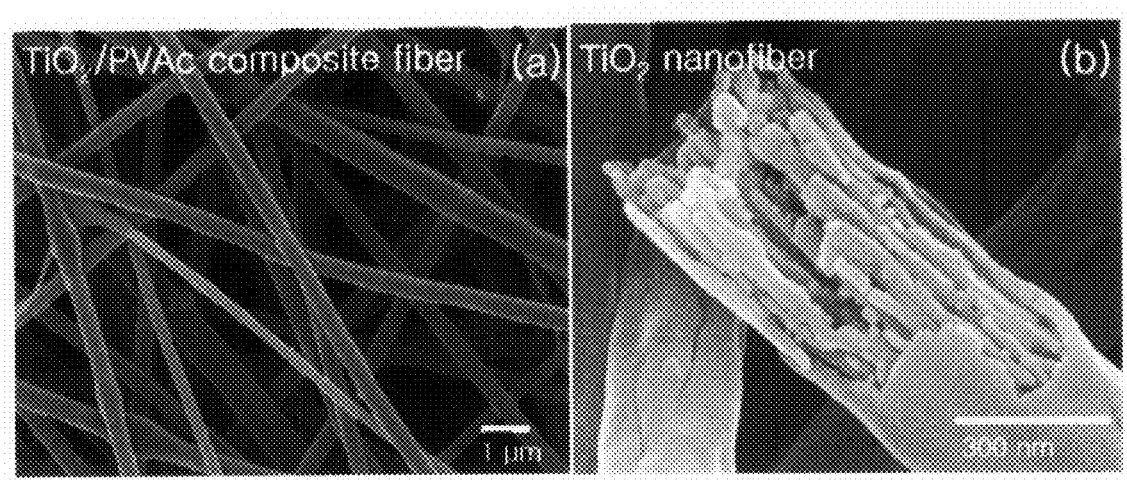
FIG. 5 illustrates (a) a SEM image of a TiO$_2$/PVAc composite fiber formed by electrospinning from a mixture solution fabricated by using a TiO$_2$ precursor and PVAc, on an interdigital capacitor (IDC) consisting of Pt electrodes on an Al$_2$O$_3$ substrate in accordance with a preferred embodiment of the present invention, (b) a SEM image of a TiO$_2$ nanofiber obtained by thermal treatment of a TiO$_2$/PVAc composite fiber at 450° C. for 30 minutes.

Next, in this comparable example, the composite fiber layer was thermally treated at 450° C. for 30 minutes in a state that thermocompression is not undergone (see FIG. 5b). FIG. 5b illustrates the state that a fiber skin surrounding fine celluloses arranged in a coaxial direction is partially peeled off, wherein the fine celluloses are generally surrounded by the fiber skin if thermal treatment is performed only without thermocompression. FIG. 5b illustrates a fiber structure having a diameter of 200 nm to 700 nm. In this case, it is noted that a macro pore between fibers has a relatively small pore volume $(V_{pore})/(cm^3 g^{-1})$. A specific surface area of the one-dimensional $TiO_2$ nanofiber thin layer, which does not have the above-described nanorod structure, was measured as 31.22 $m^2/g$ by nitrogen adsorption/desorption.

COMPARABLE EXAMPLE 2

Thermal Treatment without Thermocompression after Electrospinning of a Mixture Solution of Polyvinyl Acetate and ZnO Precursor A polymer solution obtained by dissolving polyvinyl acetate (Mw: 1,000,000) of 2.4 g in dimethylformamide of 15 ml for one day is mixed with a solution obtained by dissolving zinc acetate of 6 g in dimethylformamide of 15 ml. At this time, acetic acid of 2 g is reacted as a catalyst for the sol-gel reaction while being stirred for two hours. The precursor in which the reaction has been made is transferred into syringe and mounted on the electrospinning device. Afterwards, a voltage is applied between a tip provided in the end of the syringe and the substrate (in this case, sensor electrode) to obtain an ultrafine ZnO-polyvinylacetate composite fiber layer (see FIG. 12a). In this case, the voltage is 15 kv, the flow rate is 15 μl/min, the total discharge amount is 500 to 5,000 μl, and the distance between the tip and the substrate is 10 cm. Especially, it is observed that a fine structure of the ZnO nanofiber is changed depending on the content of the acetic acid used for the sol-gel reaction.

Figure 12:
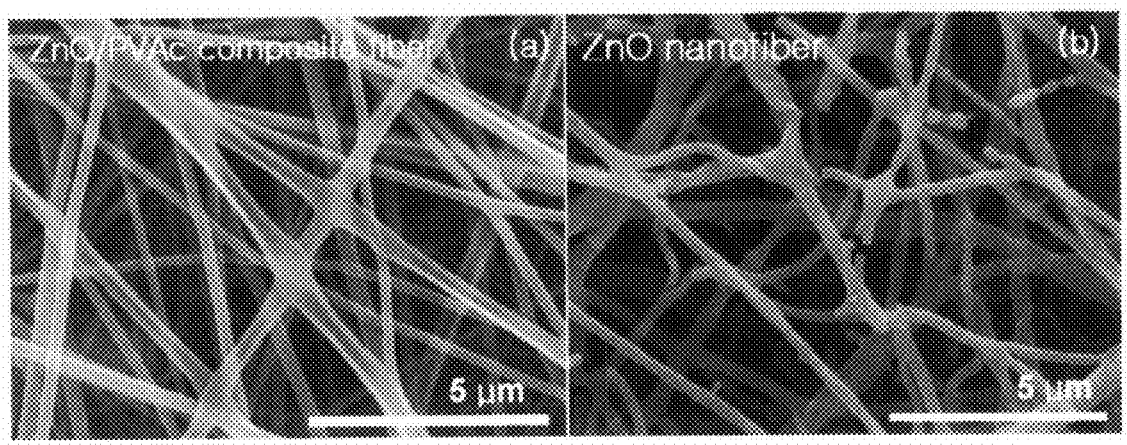
FIG. 12 illustrates (a) a SEM image of a ZnO/PVAc composite fiber formed by electrospinning from a mixture solution fabricated by using a ZnO precursor and PVAc, on an interdigital capacitor (IDC) consisting of Pt electrodes on an Al$_2$O$_3$ substrate, (b) a SEM image of a ZnO nanofiber obtained by thermal treatment of a ZnO/PVAc composite fiber at 450° C. for 30 minutes.

Next, in this comparable example, the ZnO/PVAc composite fiber layer was thermally treated at 450° C. for 30 minutes in a state that thermocompression is not undergone (see FIG. 12b). FIG. 12b illustrates a fiber structure having a diameter of 200 nm to 700 nm. In this case, it is noted that a macro pore between fibers has a relatively small pore volume $(V_{pore})/(cm^3 g^{-1})$.

COMPARABLE EXAMPLE 3

Thermal Treatment without Thermocompression after Electrospinning of a Mixture Solution of Polyvinyl Acetate and $SnO_2$ Precursor A polymer solution obtained by dissolving polyvinyl acetate (Mw: 1,000,000) of 2.4 g in dimethylformamide of 15 ml for one day is mixed with a solution obtained by dissolving tin acetate of 6 g in dimethylformamide of 15 ml. At this time, the solution is transparent and has a little yellow color. Then, acetic acid of 2 g is reacted as a catalyst for the sol-gel reaction while being stirred for two hours. The transparent precursor in which the reaction has been made is transferred into a syringe and mounted on the electrospinning device. Afterwards, a voltage is applied between a tip provided in the end of the syringe and the substrate to obtain a $SnO_2$-polyvinylacetate composite fiber layer (see FIG. 17a). In this case, the voltage is 12 kv, the flow rate is 30 μl/min, the total discharge amount is 500 to 5,000 μl, and the distance between the tip and the substrate is 10 cm. Especially, it is observed that a fine structure of the $SnO_2$ nanofiber is changed depending on the content of the acetic acid used for the sol-gel reaction.

Figure 17:
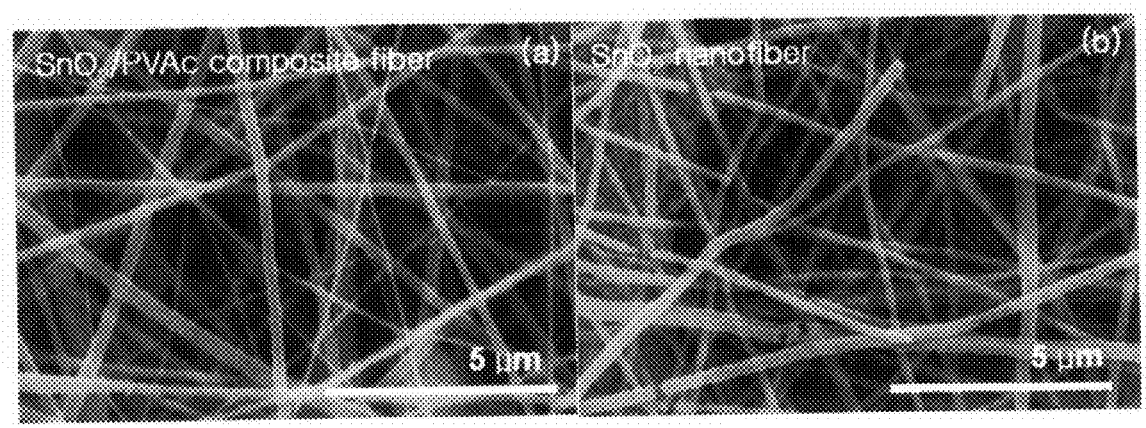
FIG. 17 illustrates (a) a SEM image of a SnO$_2$/PVAc composite fiber formed by electrospinning of a mixture solution fabricated by using a SnO$_2$ precursor and PVAc, on an interdigital capacitor (IDC) consisting of Pt electrodes on an Al$_2$O$_3$ substrate, (b) a SEM image of a SnO$_2$ nanofiber obtained by thermal treatment of a SnO$_2$/PVAc composite fiber at 450° C. for 30 minutes.

Next, in this comparable example, the $SnO_2$/PVAc composite fiber layer was thermally treated at 450° C. for 30 minutes in a state that thermocompression is not undergone (see FIG. 17b). FIG. 17b illustrates a fiber structure having a diameter of 200 nm to 700 nm. In this case, it is noted that a macro pore between fibers has a relatively small pore volume $(V_{pore})/(cm^3 g^{-1})$.

EXAMPLE 1

Fabrication of Fiber of Single Crystalline Nanorod Structure by Thermocompression and Post Heat-Treatment of $TiO_2$-Polyvinylacetate Composite Fiber Layer of Comparable Example 1

The polymer and $TiO_2$ precursor were mixed in the $TiO_2$-polyvinylacetate composite fiber layer fabricated by the electrospinning of the comparable example 1. To fabricate the nanorods of the present invention, which have excellent thermal, mechanical and electrical stability, the substrate on which the polymer-$TiO_2$ composite fiber had been laminated was compressed in a press heated at 120° C. with 1.5 $kgf/cm^2$ (213.4 psi) for 10 minutes, thereby separating the $TiO_2$ celluloses formed by the electrospinning. In other words, the fiber skin surrounding the fine cellulose shown in FIG. 5(b) is pulverized to separate the $TiO_2$ celluloses. Referring to FIG. 6(a), it is noted that after the composite fiber layer is compressed, the plasticized polyvinylacetate is partially transformed to form an interconnected film. In other words, the polyvinylacetate having a low glass transition temperature is partially or totally melted to be tightly attached to the substrate. This is needed to increase adhesion with the substrate.

The thermally-compressed substrate was thermally treated at 450° C., and the polyvinylacetate contained in the fiber layer was thermally dissolved, thereby obtaining a porous metal oxide thin layer having a network structure of nanofibers containing nano-rod, as shown in FIG. 6(b). The porous metal oxide thin layer increases the specific surface area and has excellent adhesion strength with the substrate to obtain excellent electrical contact and excellent thermal and mechanical stability.

Figure 7:
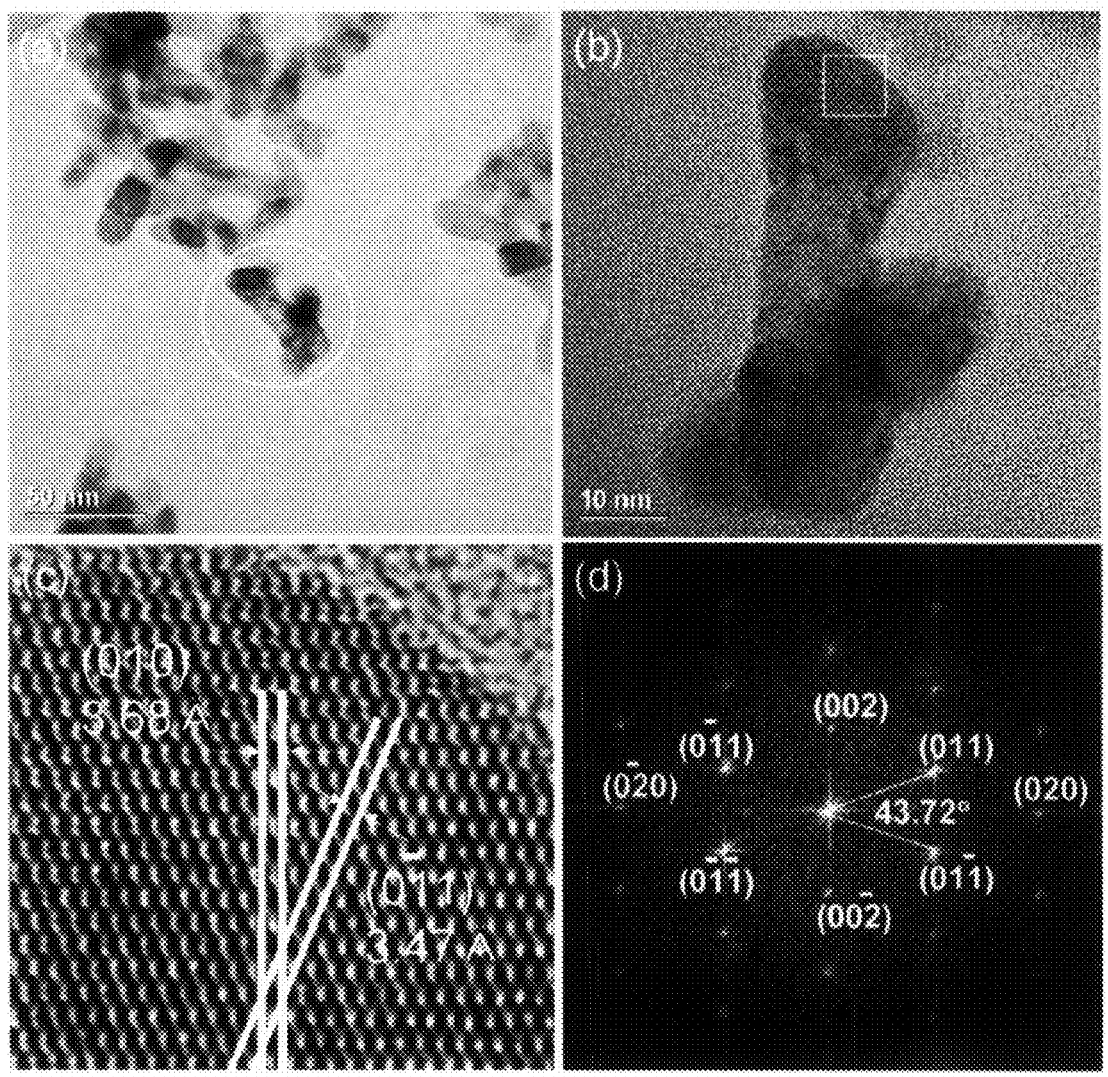
FIG. 7 illustrates (a) a TEM image of a TiO$_2$ nanorod generated by thermal treatment after melting of polymer through thermocompression, (b) a TiO$_2$ nanorod having a single crystalline structure in the range of width 10 nm to 20 nm and length of 50 nm to 100 nm, (c) lattice image of a single crystalline TiO$_2$ nanorod and (d) Fourier transform (FFT) electron diffraction pattern showing a single crystalline TiO$_2$ nanorod having an anatase structure.

FIGS. 7(a) and (b) illustrate TEM images of a single crystalline $TiO_2$ nanorod having an average width of 10~20 nm and an average length of 50~100 nm. Through the lattice image and the FFT electron diffraction pattern shown in FIGS. 7c and 7d, it is noted that the single crystalline $TiO_2$ nanorod has an anatase structure.

Figure 8:
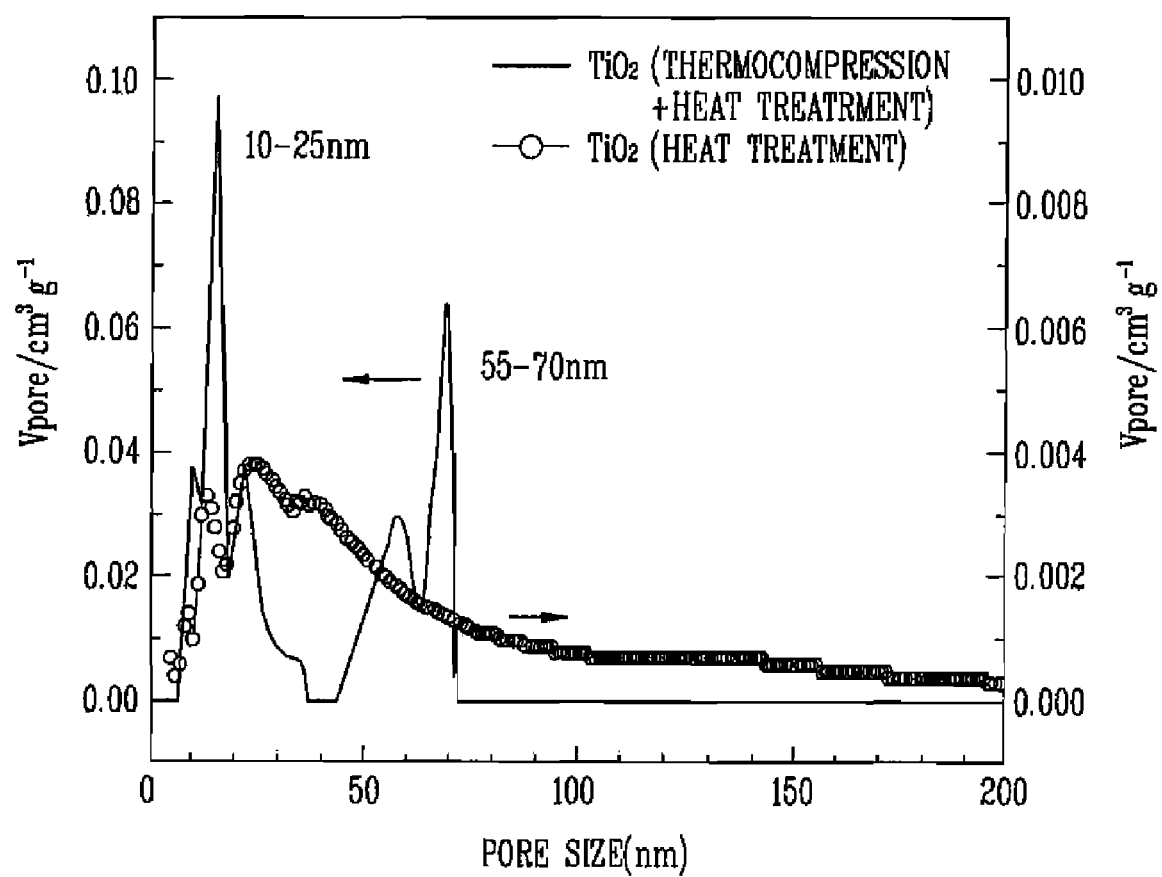
FIG. 8 is a graph illustrating distribution in size of a pore obtained through BET analysis of a TiO$_2$ nanofiber thermally treated through thermocompression and a TiO$_2$ nanofiber thermally treated without thermocompression.

FIG. 8 is a graph illustrating distribution in size of a pore obtained through BET analysis of a $TiO_2$ nanofiber thermally treated through thermocompression and a $TiO_2$ nanofiber thermally treated without thermocompression. It is noted that the $TiO_2$ nanofiber thermally treated without thermocompression has a specific surface area of 31.22 $m^2/g$ while the $TiO_2$ nanofiber thermally treated through thermocompression has a high specific surface area of 138.23 $m^2/g$ through the nanorod structure. Especially, the greater porous volume is formed through distribution of the nanorods, and the bimodal pore distribution of 10-25 nm and 55-70 nm is formed, whereby a fast gas diffusion path is obtained to increase sensitivity of the sensor. In this case, a small pore is formed between nanorods, and a great pore is formed between nanofibers.

EXAMPLE 2

Fabrication of Fiber of Single Crystalline Nanograin Twisted by Thermocompression and Post Heat-Treatment of ZnO-Polyvinylacetate Composite Fiber Layer of Comparable Example 2

The polymer and ZnO precursor were mixed in the ZnO-polyvinylacetate composite fiber layer fabricated by the electrospinning of the comparable example 2. To fabricate the nanofiber containing nanograin according to the present invention, which has excellent thermal, mechanical and electrical stability, the substrate on which the polymer-ZnO composite fiber had been laminated was compressed in a press heated at 120° C. with 1.5 $kgf/cm^2$ (213.4 psi) for 10 minutes. FIG. 13(a) illustrates ZnO/PVAc composite fibers connected with each other by melting of PVAc, occurring during thermocompression. In other words, the polyvinylacetate having a low glass transition temperature is totally melted to be tightly attached to the substrate. This is needed to increase adhesion with the substrate.

The thermally-compressed substrate was thermally treated at 450° C., and the polyvinylacetate contained in the fiber layer was thermally dissolved, thereby obtaining a porous metal oxide thin layer having a network structure of nanofibers containing twisted single crystalline nano-grains as shown in FIG. 13(b). The porous metal oxide thin layer increases the specific surface area and has excellent adhesion strength with the substrate to obtain excellent electrical contact and excellent thermal and mechanical stability.

FIGS. 13(c) and (d) illustrate magnified images of FIG. 13(b), illustrating nanofibers composed of nanograins conglomerated in the range of 20 nm (average size of 10~50 nm), having a fine single crystalline twisted structure. In case of the nanofiber composed of nano-grains, fine pores that provide a fast gas diffusion path and the volume of a grain boundary increase, thereby obtaining high gas sensitivity. In this case, the ZnO thin layer includes macro pores between nanofibers and meso pores between nanograins, wherein the average size of the macro pore is in the range of 100 nm, and the average size of the meso pore is in the range of 1~25 nm. It is observed from actual BET analysis that the macro pore has a lower pore $V_{pore}$ than the meso pore due to a considerably low pore volume ($V_{pore}/cm^3g^{-1}$). Accordingly, the macro pore greatly serves to improve sensor characteristics but to less improve sensitivity of the sensor than the meso pore.

Figure 14:
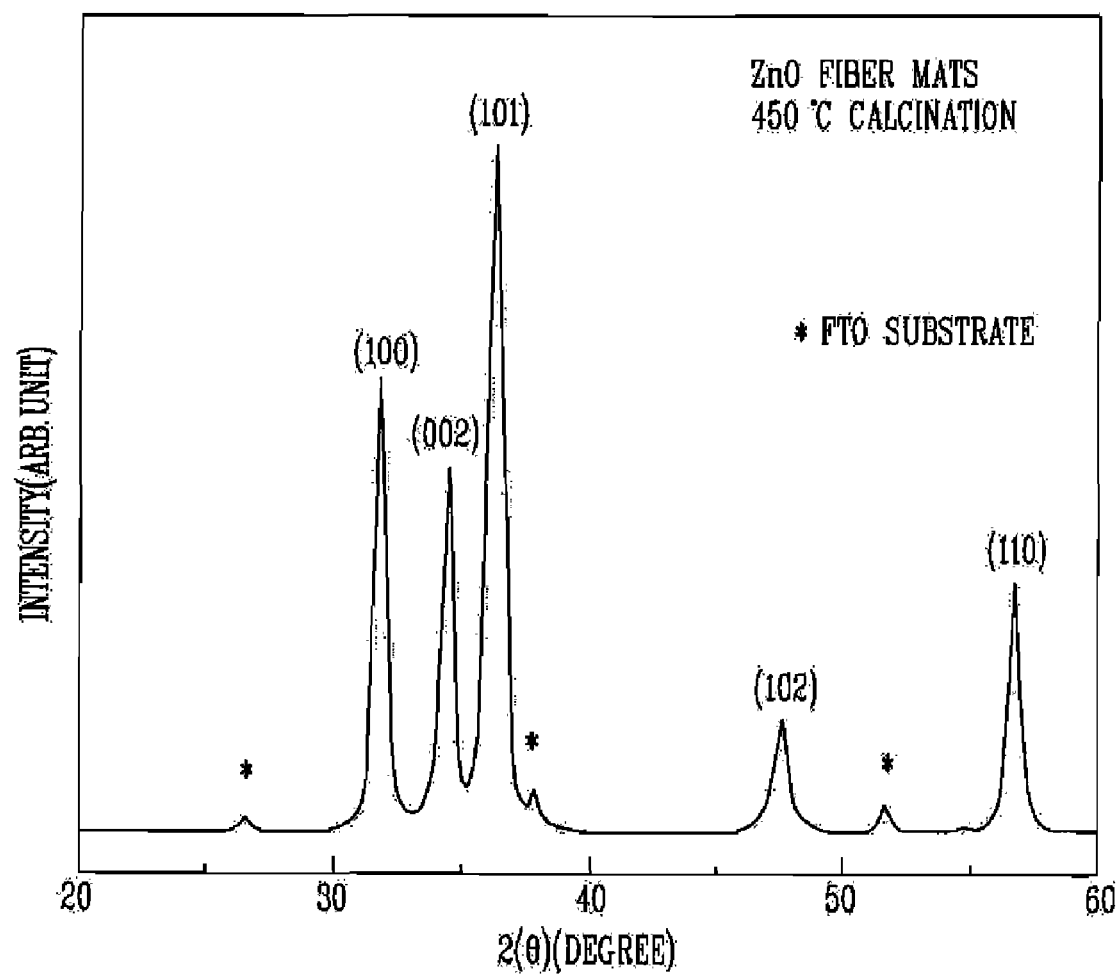
FIG. 14 illustrates is a graph illustrating X-ray diffraction pattern characteristics of ZnO having a surface structure of FIG. 13(b)
Figure 15:
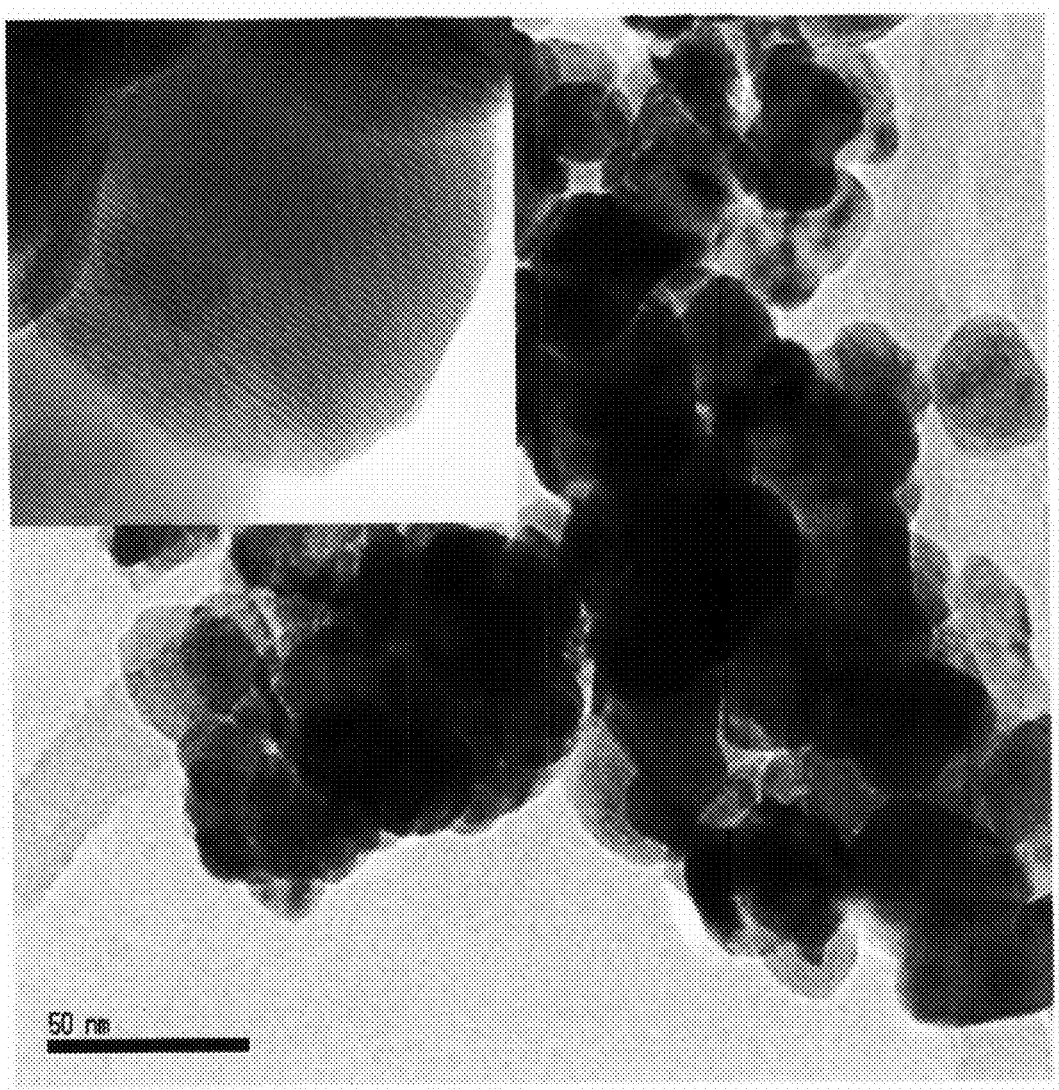
FIG. 15 illustrates a TEM image of ZnO thermally treated after thermocompression of FIG. 13(d), wherein nano grains of FIG. 13(d) have a ZnO single crystalline structure.

Furthermore, as shown in X-ray diffraction characteristics of FIG. 14, it is noted that ZnO has a single phase structure obtained through thermocompression and thermal treatment. Referring to TEM image of FIG. 15, single crystalline ZnO is obtained by nanograins conglomerated in the range of 20 nm (average size in the range of 10~50 nm), wherein the nanofibers illustrate a twisted structure as shown in FIGS. 13(b), (c) and (d), which improves stability of the fiber.

EXAMPLE 3

Fabrication of Fiber of Nanorod Structure Composed of Nanograins by Thermocompression and Post Heat-Treatment of $SnO_2$-Polyvinylacetate Composite Fiber Layer of Comparable Example 3

The polymer and $SnO_2$ precursor were mixed in the $SnO_2$-polyvinylacetate composite fiber layer fabricated by the electrospinning of the comparable example 3. The substrate on which the polymer-$SnO_2$ composite fiber had been laminated was compressed in a press heated at 120° C. with 1.5 $kgf/cm^2$ (213.4 psi) for 10 minutes.

FIG. 18(a) illustrates $SnO_2$/PVAc composite fibers connected with each other by melting of PVAc, occurring during thermocompression. FIG. 18(b) illustrates continuous nanofibers of fine nanograins obtained after thermal treatment at 450° C. for 30 minutes through thermocompression. The nanofibers may show continuity as shown in FIG. 18(b) if a small content is spun. The nanofibers may show discontinuity of a nanorod structure having a length of 50~400 nm and a width of 20~200 nm as shown in FIG. 18(c) if a great content is spun. FIG. 18(d) shows that each nanorod consists of nanograins in the range of 10 nm (average size of 5~20 nm). Since the nanorod has a lot of fine pores consisting of nanograins, gas sensitivity is more improved than that of a metal oxide of ultrafine fiber structure obtained without thermocompression. As shown, pores between the nanorods and pores between nanograins are provided, wherein the pore between the nanograins has an average size of 50~80 nm and the pore between the nanorods has an average size of 1~25 nm. In other words, the pore between the nanorods and the pore between the nanograins have a fine size less than 100 nm.

Figure 19:
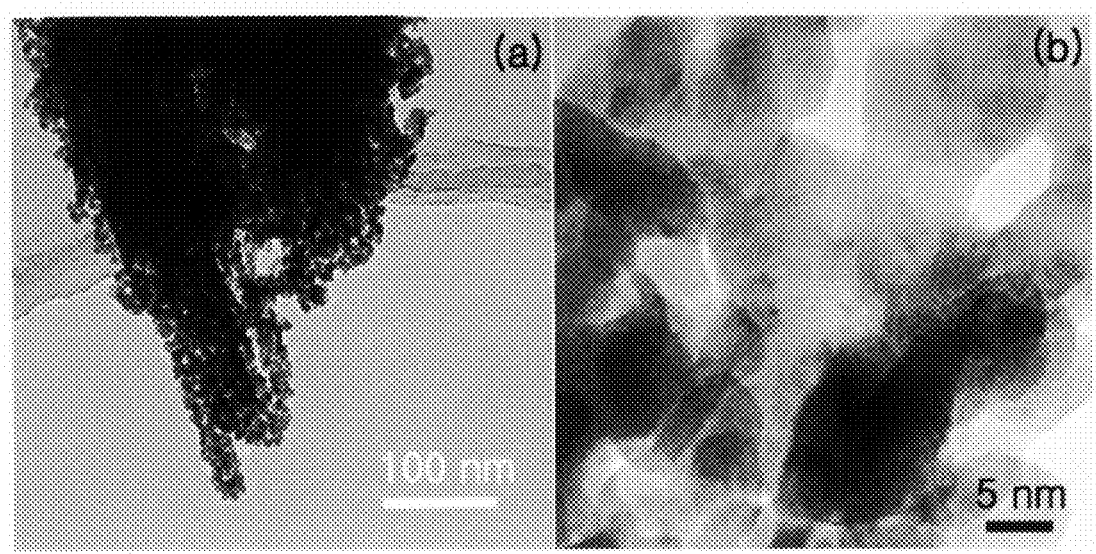
FIGS. 19(a) and (b) illustrate TEM images of SnO$_2$ thermally treated after thermocompression, having a surface structure of nanorod or nanofiber, wherein SnO$_2$ has a single crystalline structure in the range of 10 nm or so.

FIGS. 19(a) and (b) illustrate TEM images of $SnO_2$ thermally treated after thermocompression, having a surface structure of nanorod or nanofiber, the nanorod or the nanofiber consisting of nanograins, wherein FIG. 19(b) has a single crystalline structure in the range of 10 nm or so. In case of the nanofiber composed of nanograins and the nanorod composed of nanograins, fine pores that provide a fast gas diffusion path and the volume of a grain boundary increase, thereby obtaining high gas sensitivity.

EXAMPLE 4

Fabrication of Doped Metal Oxide Semiconductor Nanofiber

Various metal oxides have been introduced in the above-described examples 1~3, wherein the metal oxide precursor-polymer composite fibers were fabricated through electro-spinning, the polymer was partially or totally melted through thermocompression to improve adhesion with the substrate, and nanofiber of nanorod/nanograin type was obtained after thermal treatment.

In this example, a dopant such as a donor or an acceptor was added to the metal oxide semiconductor to control the gas response speed of the metal oxide semiconductor and change the sensor's dynamic range. The doped nanofiber includes (Nb, Fe, Co, V) doped $TiO_2$, Fe doped $SrTiO_3$ and (In, Ga) doped ZnO nanofiber added with a dopant in the range of 0.01~50 wt %.

For example, to obtain Nb doped $TiO_2$, polyvinylacetate (Mw: 1,000,000) of 2.4 g was dissolved in dimethylforma-mide (DMF) of 30 ml and mixed with titanium propoxide of 6 g. At this time, acetic acid of 2 g was reacted as a catalyst for the sol-gel reaction while being stirred for two hours. In addition, $Nb(OC_2H_5)_5$ of 0.01~3 g was further added and stirred. The precursor in which the reaction has been made was transferred into a syringe and mounted on the electro-spinning device. Afterwards, a voltage was applied between a tip provided in the end of the syringe and the substrate (in this case, sensor electrode) to obtain a fiber. In this case, the voltage is 15 kv, the flow rate is 15 μl/min, and the distance between the tip and the substrate is 10 cm. Especially, it is observed that a fine structure of the Nb-doped $TiO_2$ nanofiber is changed depending on the content of the acetic acid used for the sol-gel reaction.

FIG. 20 illustrates SEM image of Nb-doped $TiO_2$ nanofiber obtained by addition of $Nb(OC_2H_5)_5$ of 5 mM after thermo-compression and thermal treatment, wherein the nanofiber includes a nanograin or nanorod structure. It is noted from inset photograph of FIG. 20 that the nanofiber has a fine nanograin or nanorod structure. As described above, $TiO_2$ is doped with a donor such that gas response density can be controlled to change $TiO_2$ from n-type to p-type through change of gas response speed and electrical conductivity.

EXAMPLE 5

Fabrication of Ultrafine $TiO_2$ Fiber Using Polystyrene

Figure 21:
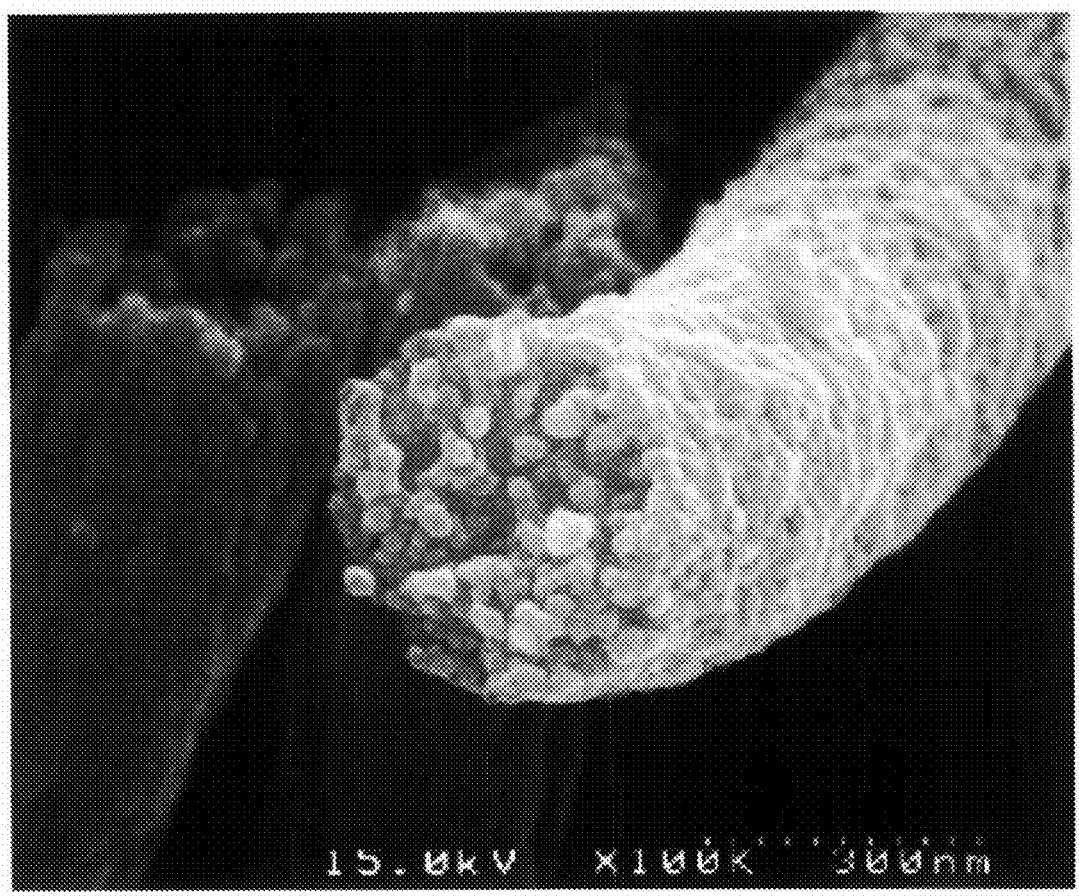
FIG. 21 illustrates a SEM image of a TiO$_2$ fiber electrospun using polystyrene (PS) instead of PVAc, obtained by thermal treatment at 450° C. for 30 minutes in accordance with the fifth embodiment of the present invention, wherein a preparation of metal oxide nanofiber is not limited to a specific polymer.

After polystyrene (Mw: 350,000 g/mol, Aldrich) was dissolved in DMF in the range of 0.25 g/mL, titanium propoxide was added in the range of 0.19 g/mL and a small content of acetic acid was added as a catalyst to perform the sol-gel reaction of titanium propoxide. Then, electrospinning was performed under the same condition as that of the comparable example 1. Afterwards, the $TiO_2$-polystyrene composite fiber was thermally treated at 450° C. to obtain a structure of $TiO_2$ fiber from which polystyrene used as a matrix was removed, as shown in FIG. 21. In this example, $TiO_2$ fiber different from $TiO_2$ nanofiber (cellulose structure having a longitudinally extended nanofiber inner structure) thermally treated without thermocompression through the comparable example 1 was formed. Also, the $TiO_2$ fiber of this example showed a structure different from the nanofibers of the above-described examples.

In other words, since polystyrene has not good miscibility with $TiO_2$-precursor, it is difficult to maintain phase equilibrium. Accordingly, a $TiO_2$ domain was rapidly solidified without phase separation unlike the above-described examples to obtain a grain type shown in FIG. 21. Although a fine structure of the fiber is not the nanorod structure, the fiber has a fine and dense nanograin structure in case of thermo-compression and thermal treatment at high temperature, whereby a grain boundary has an increased area. Accordingly, response gas is diffused desirably through the grain boundary, and a response area is increased to increase reactivity and selectivity of gas, whereby it is advantageous for application of the gas sensor.

In this example, formation of the nanofiber is not limited to the polymer having a low glass transition temperature such as polyvinylacetate but various polymers having certain viscosity and including polystyrene may be used. It is noted from this example that a porous fiber structure can be obtained, which has improved reactivity between each polymer and the metal oxide precursor, and also has an improved specific surface area along with high stability through thermocompression and thermal treatment.

EXAMPLE 6

Fabrication of $CaCu_3Ti_4O_{12}$ Nanofiber of Four Components

It was noted from the examples 1~5 that a nanofiber of metal oxide semiconductor of two components such as ZnO and $SnO_2$ and three components such as doped $TiO_2$ could be fabricated, and a fiber layer of a specific structure could be fabricated through thermocompression and post heat-treatment. Also, it was noted that another surface structure could be obtained using polystyrene not polyvinylacetate as a polymer. In this example, a nanofiber of four components, i.e., $CaCu_3Ti_4O_{12}$ (CCTO) nanofiber was fabricated, a specific fine structure was obtained through the same thermocompression, and mechanical stability was improved through increased adhesion strength.

Polyvinylacetate (Mw: 1,300,000) of 2.4 g was dissolved in DMF of 15 g for 24 hours while being stirred, thereby obtaining a polymer solution having high viscosity. After $CaCl_2$ of 0.333 g and $CuCl_2$ of 1.215 g were dissolved in DMF of 15 g, the resultant solution was stirred in the polymer solution for 10 minutes. Then, acetic acid of 2 g was added as a catalyst for the sol-gel reaction and titanium propoxide of 3.41 g was also added, and then the mixture solution was stirred for 1 hour. The prepared precursor solution was transferred into the syringe and then mounted on the electrospinning device. Afterwards, the voltage was applied between the tip provided in the end of the syringe and the lower substrate to obtain a nanofiber. In this case, the voltage is 15 kv, the flow rate is 15 μl/min, and the distance between the tip and the substrate is 10 cm. Glass substrate coated with FTO and Si-wafer coated with Pt were used as the substrate, wherein the FTO substrate was thermally treated at 450° C. and the Pt substrate was thermally treated at 800° C.

The CCTO nanofiber of four components obtained as above is shown in FIGS. 22(b) and 22(d). Referring to FIGS. 22(b) and 22(d), a fiber layer of a nanorod structure containing nanograins is formed. FIG. 22(a) illustrates a CCTO nanofiber thermally treated on the FTO substrate at 450° C. without thermocompression, and FIG. 22(b) illustrates a CCTO nanofiber thermally treated on the FTO substrate at 450° C. after thermocompression. FIG. 22(c) illustrates a CCTO nanofiber thermally treated on the Pt substrate at 450° C. without thermocompression, and FIG. 22(d) illustrates a CCTO nanofiber thermally treated on the Pt substrate at 450° C. after thermocompression.

In case of no thermocompression (FIG. 22(a)), an ultrafine fiber structure has a diameter of 200 nm to 600 nm. In case of thermal treatment after thermocompression at 120° C. for 10 minutes (FIG. 22(b)), a CCTO nanorod aggregate has a dense structure. Also, in case of no thermocompression (FIG. 22(c)), an ultrafine fiber structure is obtained, in which each gain has a great size. In case of thermal treatment after thermocompression at 120° C. for 10 minutes (FIG. 22(d)), a CCTO nanorod aggregate has a dense structure. Inset of FIG. 22(c) illustrates that grains of the CCTO nanofiber are grown through thermal treatment at 800° C.

It is noted from the nanofiber structure of the metal oxide semiconductor of four components that adhesion with the substrate was improved in case of thermal treatment through thermocompression, and a specific surface area was greatly increased. Especially, considering that a nanofiber having excellent thermal, mechanical and electrical stability can be fabricated by CCTO of a complicate structure having four components, the metal oxide semiconductor nanofiber of two components [$ZnO$, $SnO_2$, $VO_2$, $TiO_2$, $In_2O_3$, $NiO$, $MoO_3$, $Fe_2O_3$], three components [composite fiber of $SrTiO_3$ or (Nb, Fe, Co, V) doped $TiO_2$, (In, Ga) doped ZnO], and four components [Fe doped $SrTiO_3$] can be fabricated. More especially, an ultrasensitive metal oxide gas sensor can be fabricated based on nanofiber having thermal, mechanical and electrical stability through thermocompression.

EXPERIMENTAL EXAMPLE 1

Evaluation of Characteristics of Gas Sensor Using $TiO_2$ Nanofiber

Resistivity changes per temperature with varying the concentration of $NO_2$ gas from 500 ppb to 50 ppm at 300° C. were measured to identify excellent property of the gas sensor using the $TiO_2$ nanofiber network of a bundle structure of nanorods fabricated on IDC consisting of Pt electrode formed on the $Al_2O_3$ substrate in accordance with the example 1. To evaluate characteristics of the gas sensor, a sensor electrode on which the $TiO_2$ nanofiber had been formed was mounted on a quartz tube in a tube furnace. While the resistivity changes of the $TiO_2$ nanofiber thin layer by various gas changes and concentration changes were measured, a Pt/Pt—Rh (type S) thermocouple measured temperature changes. A gas flux was controlled by an MFC (Tylan UFC-1500A mass flow controller and Tylan R0-28 controller). The reaction was reversible, and the response time was shorter than 1 minute.

Figure 9:
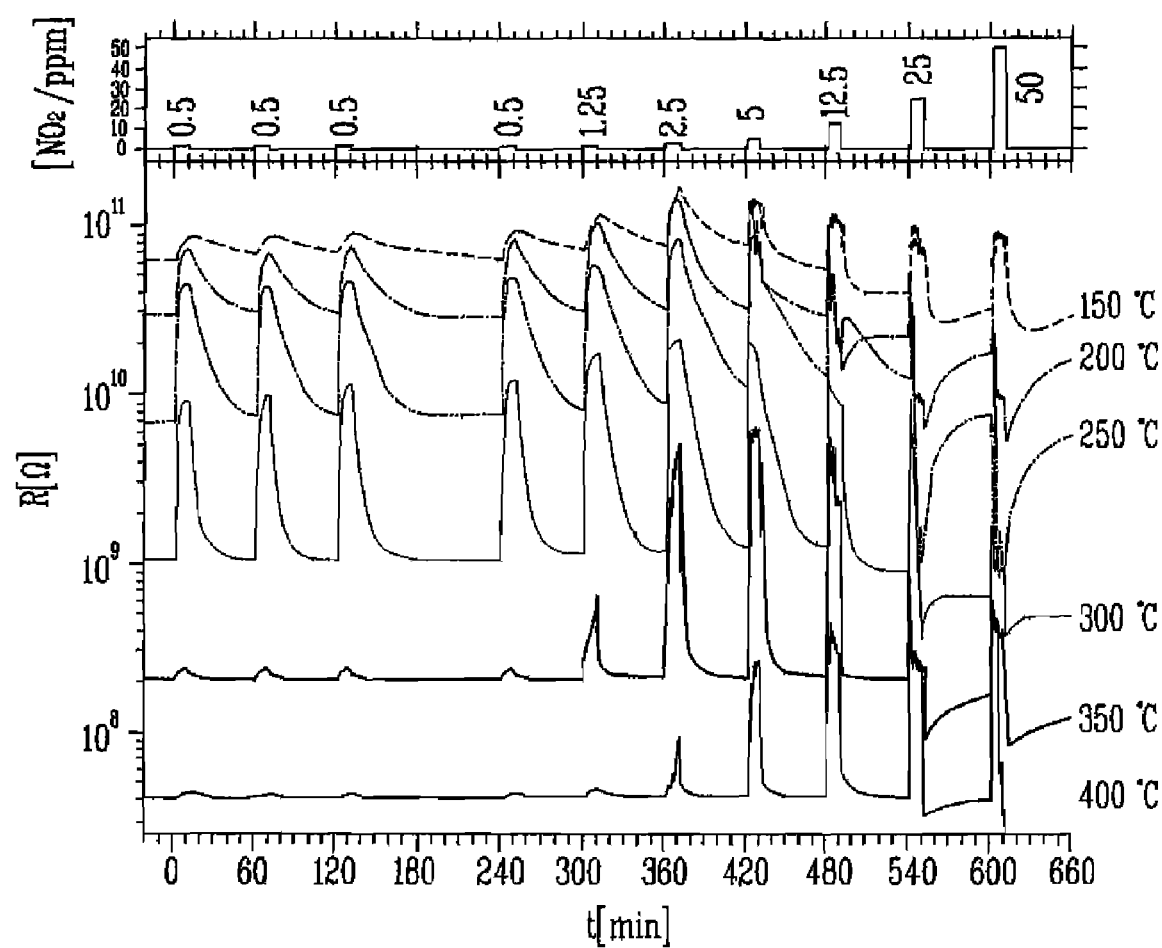
FIG. 9 illustrates a result of resistance response during cyclic exposure to 10 min pulses with increasing concentrations of NO$_2$ from 500 ppb to 50 ppm at various temperatures.
Figure 10:
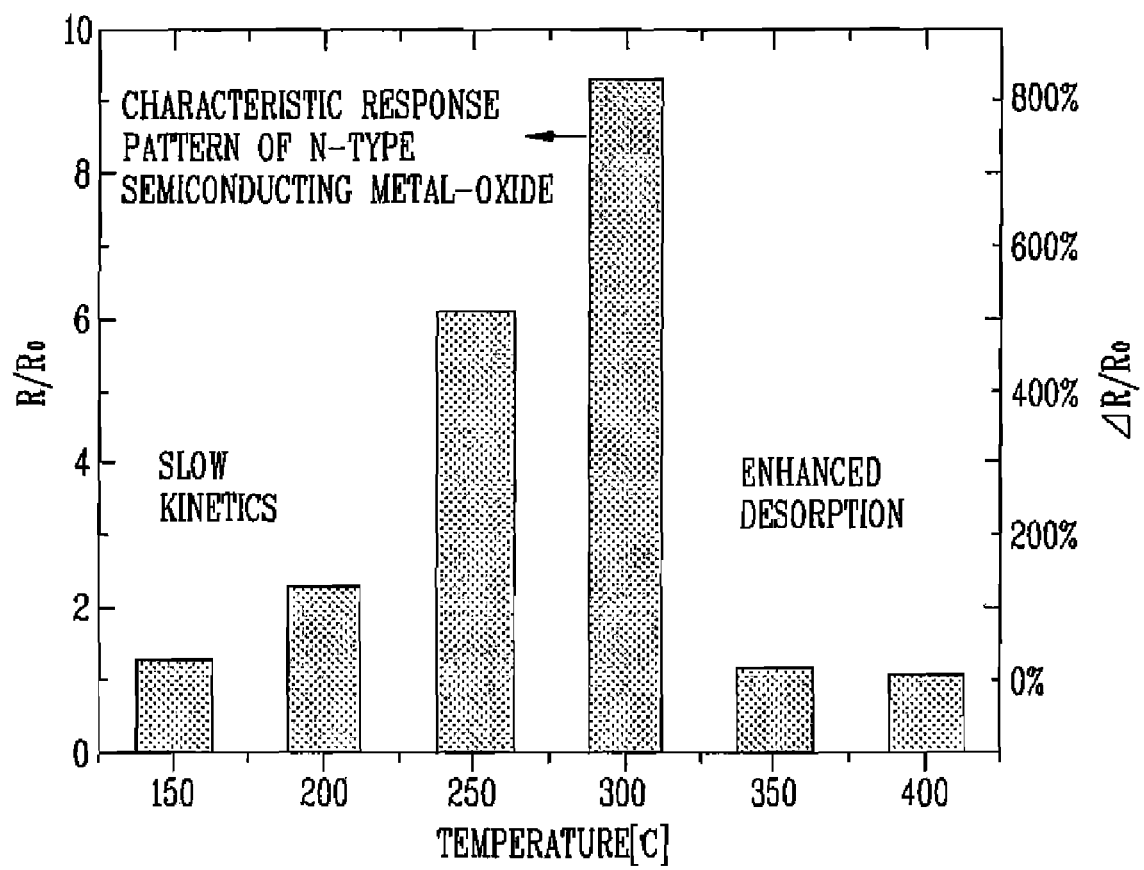
FIG. 10 is a graph illustrating sensitivity versus temperature histogram upon exposure to 500 ppb NO$_2$ in dry air.
Figure 11:
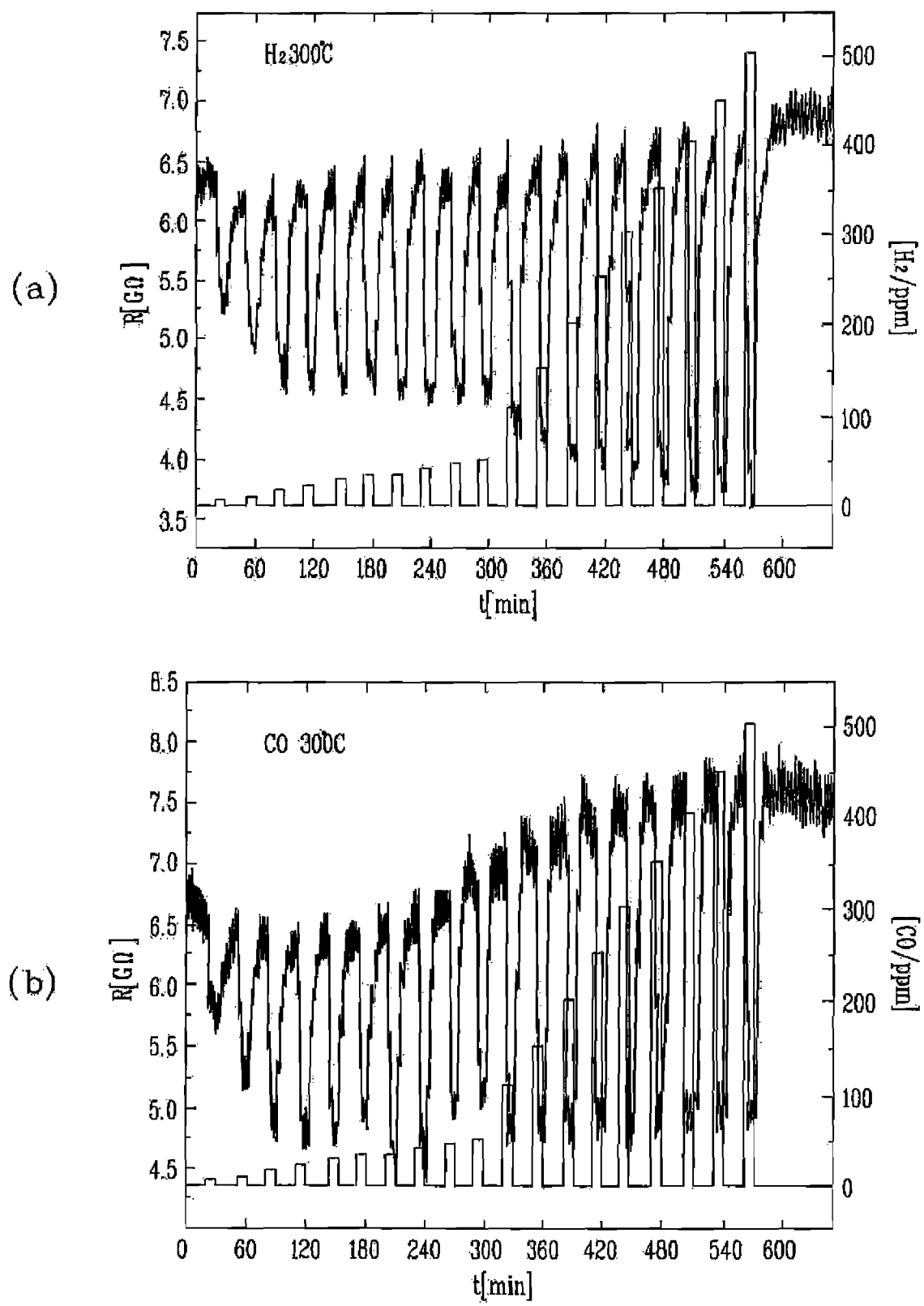
FIG. 11 illustrates (a) a resistance response of a TiO$_2$ nanofiber gas sensor measured with respect to H$_2$ gas (5 ppm to 500 ppm) at a temperature of 300° C., (b) a resistance response of a TiO$_2$ nanofiber gas sensor measured with respect to CO gas (5 ppm to 500 ppm) at a temperature of 300° C., (c) a resistance response of a TiO$_2$ nanofiber gas sensor measured with respect to CH$_4$ gas (50 ppm to 5000 ppm) at a temperature of 300° C., (d) a resistance response of a TiO$_2$ nanofiber gas sensor measured with respect to DMMP gas (8 ppm to 800 ppm) at a temperature of 300° C.
Figure 11:
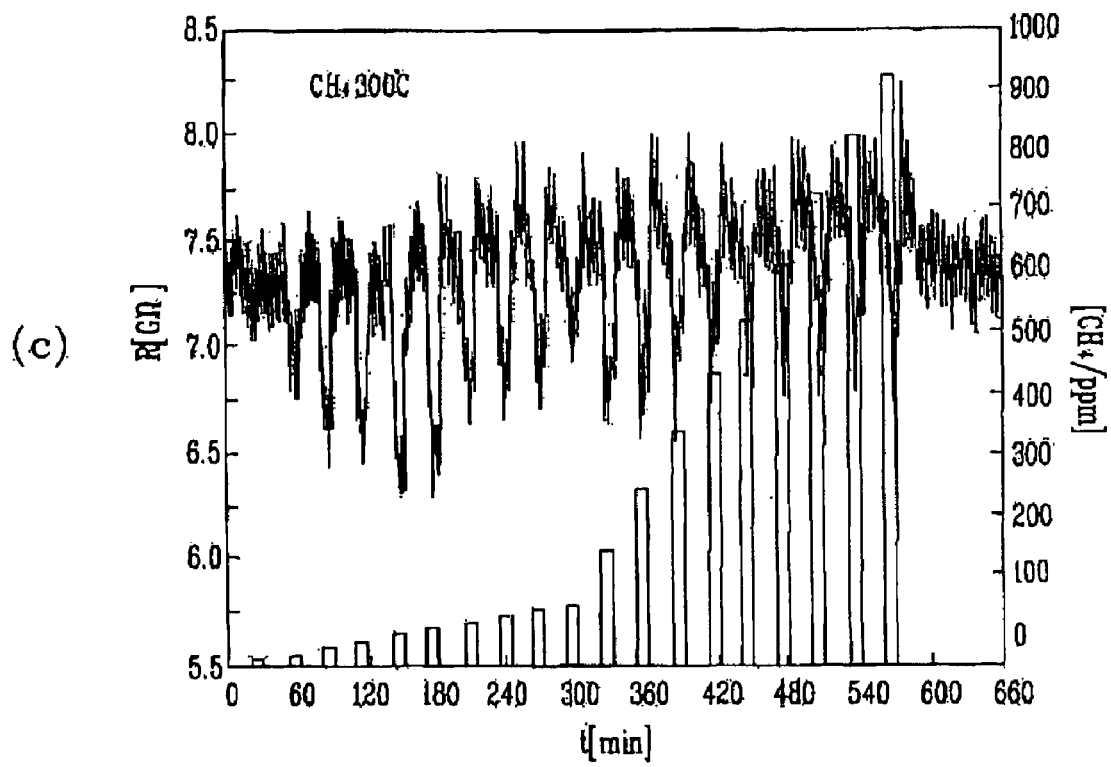
Figure 11:
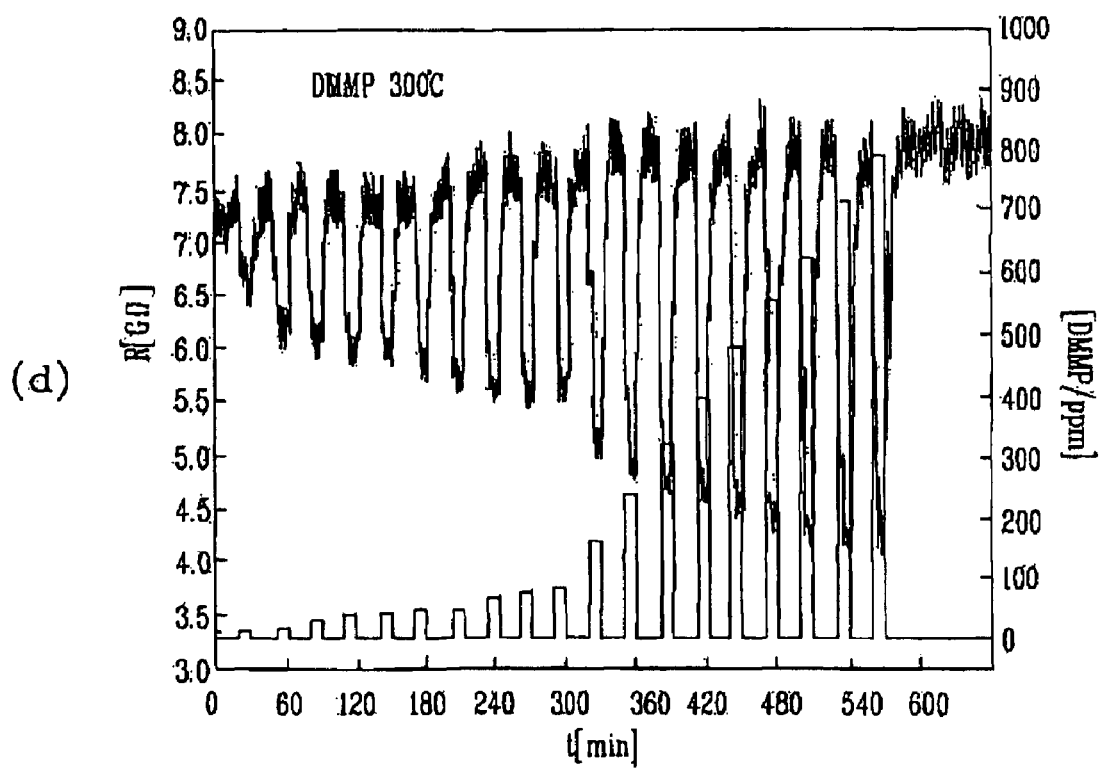

FIG. 9 illustrates a result of resistance response to cyclic exposure for 10 minutes, and FIG. 10 illustrates variation of temperature and sensitivity during $NO_2$ exposure of 500 ppb in the air. It is noted that a resistance value is increased by 833% at 300° C. during the presence of $NO_2$ of 500 ppb based on the basic resistance Ro in the air. This resultant value is 100 times higher than the result of the existing high sensitive sensor of $TiO_2$, and the concentration less than 1 ppb can be detected in case of R/Ro extrapolation. The sensor prototype made of the $TiO_2$ fiber having a fine nanorod structure had excellent $NO_2$ gas reactivity. It verified that the $TiO_2$ nanofiber could be efficiently applied to an environmental and medical gas sensor useful in $NO_2$ sensing below a sub ppm level.

Furthermore, sensor characteristics of various response gases ($H_2$, CO, $CH_4$, DMMP) are shown in FIGS. 11(a) to (d). As shown, the resistivity showed the characteristic of the typical n-type semiconductor, namely, decrease in exposure to the reducing gas ($H_2$, Co, $CH_4$, DMMP) and increase in exposure to the oxidizing gas ($NO_2$). As shown in FIG. 11, although the reaction to the reducing gas was not as high as the reaction to NOx, it still had large change values. Among the gases, sensitivity to $H_2$ and DMMP was much higher than sensitivity to CO and $CH_4$. The sensor characteristic meant that preferential selectivity existed on $H_2$ and DMMP. Especially, the reaction to DMMP (dimethyl methylphosphonate) such as a neural gas agent verified that the nanorod and nanograin type $TiO_2$ fiber thin layer could sense DMMP increase even below a single ppm level. According to the result, this sensor was expected to be used as a CWA detector in security application.

EXPERIMENTAL EXAMPLE 2

Evaluation of Characteristics of Gas Sensor Using ZnO Nanofiber

Specific resistivity changes before/after reactions to various harmful gases at 300° C. were measured by using the twisted ZnO nanofiber of nanograins fabricated on the IDC (interdigital capacitor) consisting of Pt electrode formed on the $Al_2O_3$ substrate in the Example 2. A sensor electrode on which the ZnO nanofiber had been formed was mounted in a quartz tube in a tube furnace. While the resistivity changes of the ZnO nanofiber thin layer by various gas changes and concentration changes were measured, a Pt/Pt—Rh (type S) thermocouple measured temperature changes. A gas flux was controlled by an MFC (Tylan UFC-1500A mass flow controller and Tylan R0-28 controller). The reaction was reversible, and the response time was shorter than 1 minute.

Figure 16:
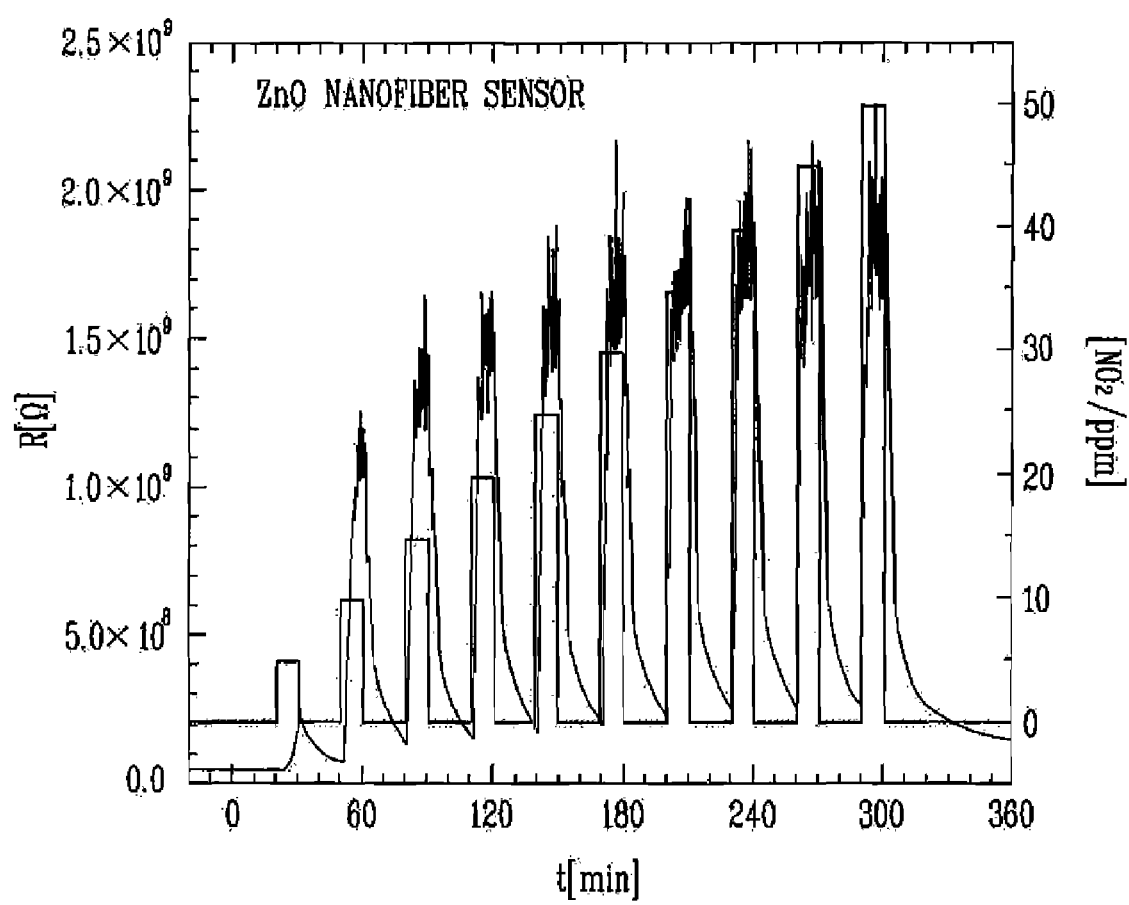
FIG. 16 illustrates a response result of a sensor having a ZnO nanofiber of a twisted structure fabricated in accordance with the second embodiment of the present invention.

As shown in FIG. 16, the resistivity showed the characteristic of the typical n-type semiconductor, namely, increase in exposure to the oxidizing gas ($NO_2$) (5~50 ppm) at 300° C. The sensor prototype made of the ZnO nanofiber having a twisted type of fine nanograins had excellent $NO_2$ gas selectivity. As shown in FIG. 16, R/Ro (R=resistivity measured in exposure to test gas and Ro=basic resistivity measured in the air) had a high value over four times (R/Ro=4 times) during a few tens ppm exposure to the air. It verified that the ZnO nanofiber could be efficiently applied to an environmental and medical gas sensor useful in $NO_2$ sensing below a sub ppm level. Thus, high sensitive gas response to various harmful gases (CO, $CH_4$, DMMP) in addition to $NO_2$ can be expected. Especially, the reaction to DMMP such as a neural gas agent or other harmful gas is expected that the ZnO fiber thin layer could sense DMMP even below a single ppm level.

Especially, the sensor using the nanofiber may be applied to $SnO_2$, $VO_2$, $TiO_2$, $In_2O_3$, $CaCu_3Ti_4O_{12}$, NiO, $MoO_3$, $SrTiO_3$, $Fe_2O_3$, $TiO_2$ doped with at least one of Nb, Fe, Co, and V, $SrTiO_3$ doped with Fe, or ZnO doped with at least one of In and Ga, in addition to $TiO_2$ and ZnO verified in the experimental examples 1 and 2. If the metal oxide semiconductor consists of nanofiber containing nanograin and/or nanorod, it can be used for the ultrasensitive sensor for sensing harmful environmental gases ($H_2$, $O_2$, CO, NOx, alcohol, $NH_3$, $CH_4$, SOx, DMMP, phenol, acetone, formaldehyde).

Since the nanofiber obtained by the present invention has a nanograin and/or nanorod structure, the specific surface area is enlarged. Especially, since the nanofiber has a fine porous structure, fast gas diffusion and fast response speed can be expected. More especially, since the metal oxide semiconductor nanofiber is prevented from being peeled off from the sensor substrate through the thermocompression corresponding to the subject feature of the present invention, thermal, electrical and mechanical stability can be improved.

EXPERIMENTAL EXAMPLE 3

Surface Change after Thermocompression or Thermal Pressurization of Metal Oxide Semiconductor-Polymer Composite Fiber Layer It has been described in the aforementioned examples 1~3 that polyvinylacetate was partially or totally melted to obtain a composite fiber layer having a tightly closed structure with electrode as a $TiO_2$-polyvinylacetate, ZnO-polyvinylacetate, or $SnO_2$-polyvinylacetate composite fiber was thermally compressed at a temperature more than a glass transition temperature of the polymer. FIG. 6(a) illustrates SEM image of the composite fiber after the $TiO_2$-polyvinylacetate composite fiber layer is thermally compressed at a temperature more than the glass transition temperature. Also, FIG. 13(a) illustrates SEM image of the composite fiber after the ZnO-polyvinylacetate composite fiber layer is thermally compressed at a temperature more than the glass transition temperature, and FIG. 18(a) illustrates SEM image of the composite fiber after the $SnO_2$-polyvinylacetate composite fiber layer is thermally compressed at a temperature more than the glass transition temperature. Referring to FIGS. 6(a), 13(a) and 18(a), the polymer, i.e., polyvinylacetate is partially or totally melted to obtain a specific structure after thermal treatment.

The melting step of the polymer is not limited to polyvinylacetate but applied to the above-mentioned polymers. Even if electrospinning is performed using the above-mentioned polymers in addition to polyvinylacetate, adhesion is greatly increased through thermocompression before and after the glass transition temperature of each polymer, whereby a nanograin and/or nanorod type fiber layer having excellent mechanical stability can be formed. In addition, various metal oxide semiconductor nanofibers such as $WO_3$, $TiO_2$, $In_2O_3$, $VO_x$, $CaCu_3Ti_4O_{12}$, NiO, $MoO_3$, $SrTiO_3$, and $Fe_2O_3$ as well as ZnO and $SnO_2$ are fabricated in an array type through changes of the metal oxide semiconductor precursors, accuracy of sensor response can be improved.

The present invention has introduced thermocompression to solve the problem relating to poor device characteristics due to low adhesion strength between the metal oxide obtained by the existing electrospinning and the lower substrate. The metal oxide obtained after such thermocompression increases adhesion with the substrate, and induces formation of the fiber layer containing a specific type nanorod and/or nanograin structure through partial or total melting of the used polymer. As a result, the specific surface area increases and fast gas diffusivity through fine pores can be obtained, whereby the gas sensor having the fast response time and high sensitivity can be obtained. Since various metal oxide nanofibers are arrayed, it is expected that gas selectivity would be improved.

Especially, the present invention is not limited to the specific type polymer, solvent or metal oxide semiconductor precursor but applied to various kinds of metal oxide semiconductors. The ultra-sensitive sensor can be obtained to overcome limitation of the existing thin film sensor, such as low specific surface area and low response time).

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A method for fabricating an ultra-sensitive metal oxide gas sensor, comprising the steps of:
   spinning a mixture solution including a metal oxide precursor and a polymer onto a sensor electrode to form a metal oxide precursor-polymer composite fiber;
   thermally compressing or thermally pressurizing the composite fiber; and
   thermally treating the thermally compressed or thermally pressurized composite fiber to remove the polymer from the composite fiber.

2. The method as claimed in claim 1, wherein the metal oxide precursor includes a precursor constituting ZnO, $SnO_2$, $VO_2$, $TiO_2$, $In_2O_3$, $CaCu_3Ti_4O_{12}$, NiO, $MoO_3$, $SrTiO_3$, $Fe_2O_3$ through thermal treatment at a temperature more than 200° C., a precursor constituting $TiO_2$ doped with at least one of Nb, Fe, Co, and V, a precursor constituting $SrTiO_3$ doped with Fe, or a precursor constituting ZnO doped with at least one of In and Ga.

3. The method as claimed in claim 1, wherein a material containing at least one of Nb, Fe, Co, V, In and Ga is added to the mixture solution to control gas response time of the sensor and change a response range.

4. The method as claimed in claim 1, wherein the polymer is at least one selected from polyurethane, polyetherurethane, polyurethane copolymer, cellulose acetate, cellulose acetate butylate, cellulose acetate propionate, polymethylmethacrylate(PMMA), polymethylacrylate(PMA), polyacryl copolymer, polyvinylacatate(PVAc), polyvinyl acetate copolymer, polyvinyl alcohol(PVA), polyperfluoroacrylate(PPFA), polystyrene(PS), polystyrene copolymer, polystyrene copolymer, polyethylene oxide(PEO), poly(phenylene oxide)(PPO), polyethylene oxide copolymer, polypropylene oxide copolymer, polycarbonate(PC), polyvinyl chloride(PVC), polycaprolactone, polycaprolactone, polyvinylpyrrolidone(PVP), polyvinylfluoride, polyvinylidenfluoride copolymer, and polyamide.

5. The method as claimed in claim 1, wherein the thermally compressing step includes partially or totally melting the polymer of the composite fiber by pressurizing the polymer at a temperature more than a glass transition temperature of the polymer, so as to improve adhesion with the sensor electrode.

6. The method as claimed in claim 5, wherein the polymer is PVAc, and is pressed under the pressure of 1.5 Kgf/cm² (213.4 psi) at 120° C. for 10 minutes.

7. The method as claimed in claim 1, wherein the thermally pressurizing step includes inducing partially or totally melting of the polymer through heating at a temperature more than a glass transition temperature of the polymer for at least 10 minutes, or inducing melting of the polymer by pressurizing the polymer using compressed air having the temperature more than the glass transition temperature of the polymer.

8. The method as claimed in claim 1, wherein the thermal treatment is performed in the range of 200~800° C. depending on types of the metal oxide precursor.

9. The method as claimed in claim 1, wherein the mixture solution is electrospun or spun by electrospinning, melt-blown, flash spinning, or electrostatic melt-blown.

10. The method as claimed in claim 1, wherein the sensor electrode has at least two sets arrayed, and a mixture solution of different materials is spun on the sensor electrode of the at least two sets.

11. The method as claimed in claim 10, wherein the two sets of the sensor electrode are simultaneously thermally compressed or thermally pressurized after the mixture solution is spun thereon.

* * * * *

UNITED STATES PATENT AND TRADEMARK OFFICE
CERTIFICATE OF CORRECTION

| | |
|---|---|
| PATENT NO. | : 7,640,789 B2 |
| APPLICATION NO. | : 11/644121 |
| DATED | : January 5, 2010 |
| INVENTOR(S) | : Il-Doo Kim et al. |

It is certified that error appears in the above-identified patent and that said Letters Patent is hereby corrected as shown below:

Title Page, Item (73) should read
-- Assignee: Korea Institute of Science and Technology, Republic of Seoul (KR) --

Signed and Sealed this

Thirtieth Day of March, 2010

David J. Kappos
*Director of the United States Patent and Trademark Office*